United States Patent
Giftakis et al.

(10) Patent No.: US 8,812,098 B2
(45) Date of Patent: Aug. 19, 2014

(54) SEIZURE PROBABILITY METRICS

(75) Inventors: Jonathon E. Giftakis, Maple Grove, MN (US); Jianping Wu, Shoreview, MN (US); Dwight E. Nelson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 341 days.

(21) Appl. No.: 13/447,460

(22) Filed: Apr. 16, 2012

(65) Prior Publication Data

US 2012/0277618 A1   Nov. 1, 2012

Related U.S. Application Data

(60) Provisional application No. 61/480,158, filed on Apr. 28, 2011.

(51) Int. Cl.
| | | |
|---|---|---|
| *A61B 5/04* | (2006.01) | |
| *A61B 5/00* | (2006.01) | |
| *A61N 1/36* | (2006.01) | |
| *A61B 5/0476* | (2006.01) | |

(52) U.S. Cl.
CPC ............. *A61B 5/0476* (2013.01); *A61B 5/4836* (2013.01); *A61B 5/7275* (2013.01); *A61N 1/36064* (2013.01); *A61B 5/0031* (2013.01); *A61B 5/4812* (2013.01); *A61N 1/36135* (2013.01); *A61B 5/4094* (2013.01); *A61B 5/0022* (2013.01); *A61B 5/6868* (2013.01); *A61B 5/686* (2013.01)
USPC .................. 600/544; 600/545; 607/2; 607/45

(58) Field of Classification Search
CPC .. A61B 5/0476; A61B 5/4094; A61B 5/0482; A61N 1/36; A61N 1/3605; A61N 1/36064; A61N 1/3606
USPC ................................ 600/544, 545; 607/2, 45
See application file for complete search history.

(56) References Cited

U.S. PATENT DOCUMENTS

| | | | |
|---|---|---|---|
| 4,227,516 | A | 10/1980 | Meland et al. |
| 4,753,246 | A | 6/1988 | Freeman |
| 4,776,345 | A | 10/1988 | Cohen et al. |
| 5,299,569 | A | 4/1994 | Wernicke et al. |
| 6,157,857 | A | 12/2000 | Dimpfel |
| 6,167,298 | A | 12/2000 | Levin |
| 6,200,273 | B1 | 3/2001 | Sininger |
| 6,227,203 | B1 | 5/2001 | Rise et al. |
| 6,402,520 | B1 | 6/2002 | Freer |

(Continued)

OTHER PUBLICATIONS

Loddenkkemper, et al., "Circadian Patterns of Pediatric Seizures," Neurology 76, Jan. 11, 2011: 145-153.

(Continued)

*Primary Examiner* — Navin Natnithithadha
*Assistant Examiner* — Etsub Berhanu
(74) *Attorney, Agent, or Firm* — Medtronic, Inc.

(57) ABSTRACT

In some examples, systems, devices, and techniques for determining a particular sleep stage of a patient, determining a seizure state of the patient during the particular sleep stage, and generating a seizure probability metric for the particular sleep stage based on the sleep stage and seizure state are described. In some cases, a patient may be more susceptible to seizure events during particular sleep stages. One or more seizure probability metrics indicative of a patient's susceptibility to seizure events during a particular sleep stage may be useful in creating a patient-specific treatment regimen.

26 Claims, 9 Drawing Sheets

(56) References Cited

U.S. PATENT DOCUMENTS

| | | |
|---|---|---|
| 6,453,193 B1 | 9/2002 | Heyrend et al. |
| 6,615,076 B2 | 9/2003 | Mitra |
| 6,920,351 B2 | 7/2005 | Mitra |
| 7,006,872 B2 | 2/2006 | Gielen et al. |
| 7,089,059 B1 | 8/2006 | Pless |
| 7,120,486 B2 | 10/2006 | Leuthardt |
| 7,171,339 B2 | 1/2007 | Repucci |
| 7,257,439 B2 | 8/2007 | Llinas |
| 7,280,867 B2 | 10/2007 | Osorio et al. |
| 7,341,562 B2 | 3/2008 | Pless |
| 7,392,079 B2 | 6/2008 | Donoghue |
| 7,409,321 B2 | 8/2008 | Repucci |
| 7,532,935 B2 | 5/2009 | Maschino et al. |
| 7,577,472 B2 | 8/2009 | Li et al. |
| 7,626,015 B2 | 12/2009 | Feinstein |
| 7,668,591 B2 | 2/2010 | Lee et al. |
| 7,734,340 B2 | 6/2010 | DeRidder |
| 7,747,318 B2 | 6/2010 | John |
| 7,801,601 B2 | 9/2010 | Maschino et al. |
| 7,818,065 B2 | 10/2010 | Llinas |
| 7,819,812 B2 | 10/2010 | John |
| 7,892,182 B2 | 2/2011 | Pless |
| 7,894,890 B2 | 2/2011 | Sun et al. |
| 7,894,903 B2 | 2/2011 | John |
| 7,937,138 B2 | 5/2011 | Liley |
| 8,017,764 B2 | 9/2011 | Feinstein |
| 8,073,534 B2 | 12/2011 | Low |
| 8,078,281 B2 | 12/2011 | Foffani |
| 8,090,674 B2 | 1/2012 | Ginosar |
| 8,140,152 B2 | 3/2012 | John |
| 8,538,512 B1 * | 9/2013 | Bibian et al. .............. 600/544 |
| 2001/0003145 A1 | 6/2001 | Mori et al. |
| 2004/0073129 A1 | 4/2004 | Caldwell et al. |
| 2004/0073273 A1 | 4/2004 | Gluckman et al. |
| 2005/0033154 A1 | 2/2005 | deCharms |
| 2005/0154424 A1 | 7/2005 | Tass |
| 2005/0197560 A1 | 9/2005 | Rao et al. |
| 2005/0209512 A1 | 9/2005 | Heruth et al. |
| 2005/0215884 A1 | 9/2005 | Greicius et al. |
| 2005/0283053 A1 | 12/2005 | deCharms |
| 2006/0155348 A1 | 7/2006 | deCharms |
| 2006/0173259 A1 | 8/2006 | Flaherty |
| 2006/0212090 A1 | 9/2006 | Lozano et al. |
| 2007/0067003 A1 | 3/2007 | Sanchez |
| 2007/0123758 A1 | 5/2007 | Miesel et al. |
| 2007/0142874 A1 | 6/2007 | John |
| 2007/0149952 A1 * | 6/2007 | Bland et al. .............. 604/890.1 |
| 2007/0150025 A1 * | 6/2007 | Dilorenzo et al. .......... 607/45 |
| 2007/0191704 A1 | 8/2007 | deCharms |
| 2007/0225674 A1 | 9/2007 | Molnar et al. |
| 2007/0244407 A1 | 10/2007 | Osorio |
| 2008/0001600 A1 | 1/2008 | deCharms |
| 2008/0015459 A1 | 1/2008 | Llinas |
| 2008/0045775 A1 | 2/2008 | Lozano |
| 2008/0071150 A1 | 3/2008 | Miesel et al. |
| 2008/0077039 A1 | 3/2008 | Donnett |
| 2008/0195166 A1 * | 8/2008 | Sun et al. .................. 607/18 |
| 2008/0243022 A1 | 10/2008 | Donnett |
| 2008/0269631 A1 | 10/2008 | Denison et al. |
| 2009/0082691 A1 | 3/2009 | Denison et al. |
| 2009/0099623 A1 | 4/2009 | Bentwich |
| 2009/0105521 A1 | 4/2009 | Bentwich |
| 2009/0124919 A1 | 5/2009 | Ginosar et al. |
| 2009/0163982 A1 | 6/2009 | deCharms |
| 2009/0177144 A1 | 7/2009 | Masmanidis |
| 2009/0179642 A1 | 7/2009 | deCharms |
| 2009/0192556 A1 | 7/2009 | Wu et al. |
| 2009/0196471 A1 | 8/2009 | Goetz |
| 2009/0220425 A1 | 9/2009 | Moxon |
| 2009/0318794 A1 | 12/2009 | deCharms |
| 2009/0318826 A1 | 12/2009 | Green et al. |
| 2010/0069739 A1 | 3/2010 | deCharms |
| 2010/0100153 A1 | 4/2010 | Carlson |
| 2010/0114237 A1 | 5/2010 | Giftakis et al. |
| 2010/0121213 A1 | 5/2010 | Giftakis et al. |
| 2010/0121214 A1 | 5/2010 | Giftakis et al. |
| 2010/0121215 A1 | 5/2010 | Giftakis |
| 2010/0135553 A1 | 6/2010 | Joglekar |
| 2010/0137937 A1 | 6/2010 | John et al. |
| 2010/0241020 A1 | 9/2010 | Zaidel et al. |
| 2010/0262205 A1 | 10/2010 | DeRidder |
| 2010/0280334 A1 | 11/2010 | Carlson et al. |
| 2010/0280335 A1 | 11/2010 | Carlson et al. |
| 2010/0280336 A1 | 11/2010 | Giftakis et al. |
| 2010/0280403 A1 | 11/2010 | Erdogmus |
| 2010/0286748 A1 | 11/2010 | Midani |
| 2011/0105584 A1 | 5/2011 | Feinstein et al. |
| 2011/0130797 A1 | 6/2011 | Talathi et al. |
| 2011/0137371 A1 | 6/2011 | Giftakis et al. |
| 2011/0144716 A1 | 6/2011 | Bikson et al. |
| 2011/0184489 A1 | 7/2011 | Nicolelis et al. |
| 2011/0196446 A1 | 8/2011 | Wu et al. |
| 2011/0218454 A1 | 9/2011 | Low |
| 2011/0257715 A1 | 10/2011 | Jarosh et al. |

OTHER PUBLICATIONS

Eusebio, et al., "Resonance in Subthalamo-Cortical Circuits in Parkinson's Disease", Brain 2009, pp. 1-12.

Garrett et al., "The Importance of Being Variable," The Journal of Neuroscience, Mar. 23, 2011, 31(12): 4496-4503.

Keimel et al., "Development Proposal: A Low Cost System for fMRI and Spectroscopic Screening and Monitoring of Alzheimer's Disease", Advanced Function Biomedical Imaging, University of Minnesota, Fall 2008, Dec. 12, 2008.

Lynall et al., "Functional Connectivity and Brain Networks in Schizophrenia", J. Neuroscience, Jul. 14, 2010—30(28):9477-9487.

Pihlajamaki et al., "Functional MRI Assessment of Task-Induced Deactivation of the Default Mode Network in Alzheimer's Disease and At-Risk Older Individuals," Behavioral Neurology 21 (1) (2009) 77-91.

Sperling, et al., "Functional Alterations in Memory Networks in Early Alzheimer's Disease," Neuromol Med (2010) 12:27-43.

Van Veen, et al., "Localization of Brain Electrical Activity via Linearly Constrained Minimum Variance Spatial Filtering" IEEE Transactions on Biomedical Engineering, vol. 44, No. 9, Sep. 1997.

Westlye, et al., "Increased Hippocampal Default Mode Synchronization During Rest in Middle-Aged and Elderly APOE ε4 Carriers: Relationships with Memory Performance," The Journal of Neuroscience, May 25, 2011, 31(21): 7775-7783.

* cited by examiner

SEIZURE PROBABILITY METRICS

This application claims the benefit of U.S. Provisional Application No. 61/480,158, entitled "SEIZURE PROBABILITY METRICS," and filed on Apr. 28, 2011, the entire content of which is incorporated herein by reference.

TECHNICAL FIELD

The disclosure relates to treatment of a patient with a medical device system and, more particularly, to treatment of a seizure disorder of a patient with a medical device system.

BACKGROUND

Some neurological disorders, such as epilepsy, are characterized by the occurrence of seizures. Seizures may be attributable to abnormal electrical activity of a group of brain cells. A seizure may occur when the electrical activity of certain regions of the brain, or even the entire brain, becomes abnormally synchronized. The onset of a seizure may be debilitating. For example, the onset of a seizure may result in involuntary changes in body movement, body function, sensation, awareness or behavior (e.g., an altered mental state). In some cases, each seizure may cause some damage to the brain, which ma result in progressive loss of brain function over time.

A therapy system may be used to manage a seizure disorder of a patient, e.g., to mitigate the effects of the seizure disorder, shorten the duration of seizures, prevent the onset of seizures, or notify a patient about an onset or potential onset of a seizure. For example, attempts to manage seizures have included the delivery of electrical stimulation to regions of the brain via a medical device and/or the delivery of drugs either orally or infused directly into regions of the brain via a medical device. In some electrical stimulation systems, a medical lead may be implanted within a patient and coupled to an external or implanted electrical stimulator. The target stimulation site within the brain or elsewhere may differ between patients, and may depend upon the type of seizures being treated by the electrical stimulation system. In automatic drug delivery systems, a catheter may be implanted within a patient and coupled to an external or implanted fluid delivery device. The fluid delivery device may deliver a dose of an anti-seizure drug into the blood stream or into a region of the brain of the patient. In either case, the therapy system may deliver therapy to manage a seizure disorder of a patient continuously, at regular intervals, and/or upon the detection of some event, such as the detection of a seizure by electroencephalogram (EEG) or electrocorticogram (ECoG) sensors implanted within the brain, or at the direction of the patient or clinician.

SUMMARY

In general, the disclosure is directed in some aspects to medical therapy devices and systems configured to manage a seizure disorder of a patient. In some examples, a medical therapy system may be configured to determine a particular sleep stage of a patient and also determine a seizure state of the patient during the particular sleep stage. Based on the seizure state, a seizure probability metric for the particular sleep stage may be generated. In some examples, a seizure probability profile for the patient may be created using respective seizure probability metrics generated for a plurality of particular sleep stages of the patient.

The seizure probability metrics and the seizure probability profile may be indicative of the probability that the patient may experience a seizure during a particular sleep stage. As a result, in some examples, the seizure probability metrics and the seizure probability profile may facilitate more effective and efficient treatment of a seizure disorder of the patient by a medical therapy system. For example, patient monitoring and/or therapy delivery by a medical therapy system during a particular sleep stage may be tailored based on the patient's susceptibility to seizure events during the particular sleep stage.

In one example, the disclosure is directed to a method comprising determining that a patient is in a first sleep stage during a first period of time, determining a first seizure state of the patient, wherein the first seizure state of the patient comprises a seizure state of the patient during the first period of time, and generating a first seizure probability metric for the first sleep stage based on at least the first sleep stage and the first seizure state.

In another example, the disclosure is directed to a system comprising a processor configured to determine that a patient is in a first sleep stage during a first period of time, determine a first seizure state of the patient, wherein the first seizure state of the patient comprises a seizure state of the patient during the first period of time, and generate a first seizure probability metric for the first sleep stage based on at least the first sleep stage and the first seizure state.

In another example, the disclosure is directed to a system comprising means for determining that a patient is in a first sleep stage during a first period of time, means for determining a first seizure state of the patient, wherein the first seizure state of the patient comprises a seizure state of the patient during the first period of time, and means for generating a first seizure probability metric for the first sleep stage based on at least the first sleep stage and the first seizure state.

In another example, the disclosure is directed to a non-transitory computer-readable storage medium comprising instructions to cause one or more programmable processor to determine that a patient is in a first sleep stage during a first period of time, determine a first seizure state of the patient, wherein the first seizure state of the patient comprises a seizure state of the patient during the first period of time, and generate a first seizure probability metric for the first sleep stage based on at least the first sleep stage and the first seizure state.

In another example, the disclosure relates to a non-transitory computer-readable storage medium comprising instructions. The instructions cause a programmable processor to perform any part of the techniques described herein. Some such embodiments may comprise a non-transitory computer-readable storage medium comprising instructions to cause one or more processors to: determine that a patient is in a first sleep stage during a first period of time, determine a first seizure state of the patient, wherein the first seizure state of the patient comprises a seizure state of the patient during the first period of time, and generate a first seizure probability metric for the first sleep stage based on at least the first sleep stage and the first seizure state The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform one or more of the techniques described herein.

The details of one or more examples are set forth in the accompanying drawings and the description below. Other features, objects, and advantages of the disclosure will be apparent from the description and drawings, and from the claims.

DETAILED DESCRIPTION

Figure 1:
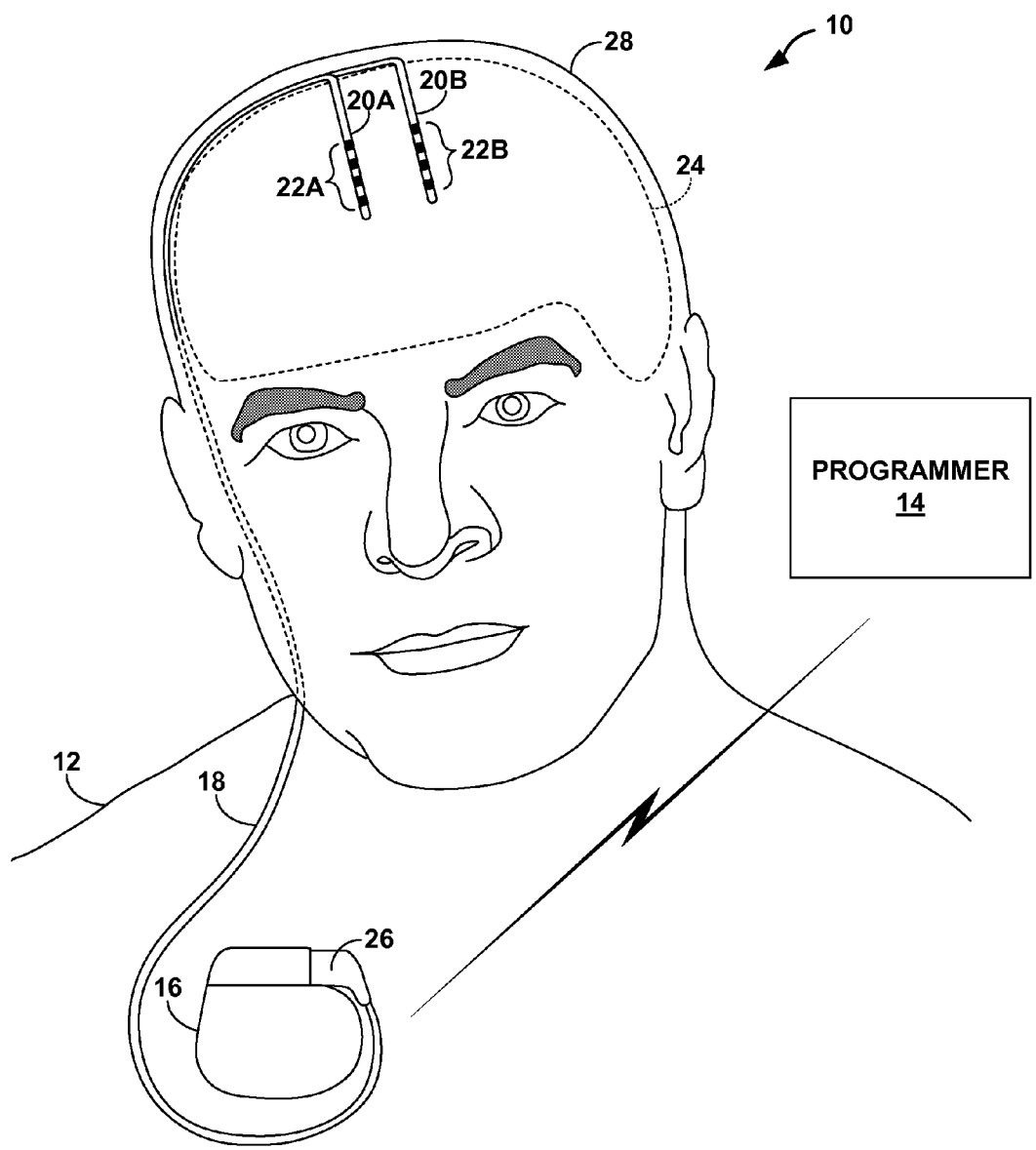
FIG. 1 is a conceptual diagram illustrating an example deep brain stimulation (DBS) system.

Some patients that suffer from seizure disorders, such as epilepsy, may be more susceptible to seizure events during particular sleep stages. That is, in some cases, a patient may be more likely to experience a seizure event during some sleep stages and less likely to experience a seizure event during other sleep stages. In some examples, a patient may experience seizures almost exclusively during sleep as a function of sleep stage. In other examples, a patient may experience seizures during time periods in which the patient is awake. In yet other examples, a patient may regularly experience seizures at specific times following a sleep-wake transition.

In some examples, a metric indicative of the patient's susceptibility to seizures during a particular sleep stage can be useful in tailoring treatment parameters for treatment of the patient's seizure disorder to the particular patient, e.g., creating a more patient-specific treatment regimen. As a result, the treatment may be more effective in treating the patient's seizure disorder because monitoring and therapy parameters may be tailored based at least partially on, e.g., when the patient has a higher or lower likelihood of experiencing a seizure event. In addition, in some examples, the treatment provided by a medical device system to manage a seizure disorder may be more efficient, e.g., because monitoring and therapy resources may be utilized according to the patient's susceptibility to experience a seizure event, instead of being utilized substantially all of the time regardless of the patient's susceptibility to a seizure event.

In accordance with one or more examples of the disclosure, a medical device system may be configured to generate a seizure probability metric for one or more sleep stages of a patient. A seizure probably metric for a particular sleep stage may be generated based on the seizure state determined for a patient during one or more instances the patient was determined to occupy the particular sleep stage. A seizure probability metric for the particular sleep stage may reflect the probability that the patient may experience a seizure during a particular sleep stage. Such a probability may be unique to the patient since the probability metric may be generated based on the determination of the seizure state of the patient while occupying the particular sleep stage on one or more previous occasions.

In some examples, a seizure probability profile may be created for the patient. The seizure probability profile may be defined by respective seizure probability metrics for each of a plurality of sleep stages of the patient. For example, the seizure probability profile may include a first seizure probability metric corresponding to a first sleep stage that quantifies the susceptibility of the patient to a seizure event during the first sleep stage. The seizure probability profile may additionally include respective seizure probability metrics corresponding to second, third, fourth, and fifth sleep stages.

In some examples, a clinician or a processor of a therapy system may determine that a patient is in a particular sleep stage and may access the seizure probability profile to identify the patient's susceptibility to a seizure event during the particular sleep stage. The clinician or processor may then adjust one or more parameters of treatment, e.g., one or more of monitoring, detection, and/or therapy delivery parameters, based on the probability of the patient experiencing a seizure during the particular sleep stage.

The patient may experience a plurality of sleep stages. In the examples described herein, the plurality of sleep stages defines the different stages of the patient's cycle of sleep and wakefulness. That is, the sleep stages may include an awake stage, as well as a plurality of stages during which the patient is sleeping or intending to sleep. For example, the plurality of sleep stages may include the awake stage, a Stage 1 sleep stage (also referred to as Stage N1 or S1), a Stage 2 sleep stage (also referred to as Stage N2 or S2), a Deep Sleep stage (also referred to as slow wave sleep), and a rapid eye movement (REM) stage. In some examples, the Deep Sleep stage may itself include multiple sleep stages, such as Stage N3 (also referred to as Stage S3) and Stage N4 (also referred to as Stage S4). During the awake stage, the patient may be conscious and able to engage in coherent cognitive and behavior responses to the external environment. During the Stage 1 sleep stage, the patient may be in the beginning stages of sleep, and may begin to lose conscious awareness of the external environment. During the Stage 2 and Deep Sleep stages, muscular activity of the patient may decrease, and conscious awareness of the external environment may disappear. During the REM sleep stage, the patient may exhibit relatively increased heart rate and respiration compared to the Stage 1, Stage 2, and Deep Sleep stages.

FIG. 1 is a conceptual diagram illustrating an example therapy system 10 that delivers therapy to manage a seizure disorder (e.g., epilepsy) of patient 12. Patient 12 ordinarily will be a human patient. In some cases, however, therapy system 10 may be applied to other mammalian or non-mammalian, non-human patients. While seizure disorders are primarily referred to herein, in other examples, therapy system 10 may also provide therapy to manage symptoms of other patient conditions in addition to a seizure disorder, such as, but not limited to, psychological disorders, movement disorders, or other neurodegenerative impairments.

Therapy system 10 may be used to manage the seizure disorder of patient 12 by, for example, minimizing the severity of seizures, shortening the duration of seizures, minimizing the frequency of seizures, preventing the onset of seizures, and the like via the delivery of therapy to patient 12. Therapy system 10 includes external programmer 14, implantable medical device (IMD) 16, lead extension 18, and one or more leads 20A and 20B with respective sets of electrodes 22A and 22B. Selected electrodes 22A, 22B may deliver therapy to patient 12 and may also, in some examples, sense bioelectrical brain signals within brain 24 of patient 12.

In the example illustrated in FIG. 1, IMD 16 includes a therapy module that comprises a stimulation generator that generates and delivers electrical stimulation therapy to patient 12 via a subset of electrodes 22A and 22B of leads 20A and 20B, respectively. As illustrated in FIG. 1, electrodes 22A, 22B of leads 20A, 20B are positioned to deliver electrical stimulation to a tissue site within brain 24, such as a deep brain site under the dura mater of brain 24 of patient 12. In some examples, delivery of stimulation to one or more regions of brain 24, e.g., an anterior nucleus (AN), thalamus, or cortex of brain 24, may provide an effective treatment to manage a seizure disorder. The specific target tissue sites can vary depending on the particular patient 12 which therapy system 10 is implemented to treat, and the type of seizure disorder afflicting patient 12.

In some examples, in the case of a seizure disorder, leads 20 may be implanted to deliver electrical stimulation to regions within the Circuit of Papez, such as, e.g., the anterior thalamic nucleus, the internal capsule, the cingulate, the fornix, the mammillary bodies, the mammillothalamic tract (mammillothalamic fasciculus), and/or hippocampus. The regions of the brain 28 within the Circuit of Papez are believed to be involved in the generation and spread of seizure activity. The Circuit of Papez is one of the major pathways of the limbic system, and the regions of brain 24 within the Circuit of Papez includes the AN, internal capsule, cingulate, HC, fornix, entorhinal cortex, mammillary bodies, and mammillothalamic tract (MMT). The regions of brain 24 within the Circuit of Papez may be considered to be functionally related (also referred to herein as functionally connected), such that activity within one part of the Circuit of Papez may affect activity within another part of the Circuit of Papez. In this way, the delivery of stimulation to one region (e.g., the AN) of the Circuit of Papez may affect the brain activity level within another region of the Circuit of Papez (e.g., the HC).

In some examples, electrodes 22A, 22B are implanted to deliver electrical stimulation therapy generated via stimulation generator of IMD 16 to and/or monitor bioelectrical brain signals within one or more regions of the brain in the Circuit of Papez, such as, e.g., the AN, the internal capsule, the cingulate, the fornix, the mammillary bodies, the mammillothalamic tract, and/or HC. In some examples, a disorder of patient 12 may be effectively managed by controlling or influence the brain activity level within one or more regions of the Circuit of Papez. For example, with respect to seizure disorders, therapy may be delivered from IMD 16 to regions within the Circuit of Papez to suppress brain activity (also referred to as cortical activity) within regions of the Circuit of Papez, such as, e.g., the HC. Suppression of brain activity within the HC via therapy may reduce the likelihood of a seizure by patient 12.

Processor 42 may control stimulation generator 44 according to one or more therapy programs stored in memory 40 to apply particular stimulation parameter values specified by one or more programs, such as amplitude, pulse width, and pulse rate. In some examples, stimulation generator 44 generates and delivers stimulation signals to anterior nucleus of the thalamus of brain 28 of patient 12 via a select combination of electrodes 22A, 22b, where the stimulation signals have a frequency in a range of about 3 Hertz (Hz) to about 250 Hz, a voltage of about 0.1 volts to about 10.5 volts, and a pulse width of about 60 microseconds to about 450 microseconds. In some examples, the stimulation signals have a frequency of 120 Hz, a voltage of about 4 volts, and a pulse width of about 100 microseconds. In addition, in some examples, the stimulation signals have a frequency of 145 Hz, a voltage of about 5 volts, and a pulse width of about 145 microseconds. In addition, the stimulation signals may have any suitable therapy cycle, which includes an on-cycle during which therapy is delivered to patient 12 and an off-cycle during which therapy is not delivered to patient 12. For example, a therapy cycle may have an on-cycle of about thirty seconds to about five minutes (e.g., about one minute) and an off-cycle of about thirty seconds to about five minutes (e.g., about five minutes).

Other stimulation targets within brain 28, other stimulation parameter values, and other therapy cycles are contemplated. Other ranges of therapy parameter values may also be useful, and may depend on the target stimulation site within patient 12, which may or may not be within brain 28. While stimulation pulses are described, stimulation signals may be of any form, such as continuous-time signals (e.g., sine waves) or the like.

In the example illustrated in FIG. 1, therapy system 10 includes a sensing module that senses bioelectrical signals within brain 24 of patient 12. The bioelectrical brain signals may reflect changes in electrical current produced by the sum of electrical potential differences across brain tissue. Examples of bioelectrical brain signals include, but are not limited to, an EEG signal, an ECoG signal, a local field potential (LFP) sensed from within one or more regions of a patient's brain, and action potentials from single cells within the patient's brain. In addition, in some examples, a bioelectrical brain signal includes a signal indicative of the measured impedance of tissue of brain 24 over time. In some examples, IMD 16 includes the sensing module, which senses bioelectrical signals within brain 24 via a subset of electrodes 22A, 22B. Examples in which IMD 16 senses bioelectrical signals within brain 24 are described herein. However, in other examples, the sensing module that senses bioelectrical signals within brain 24 can be physically separate from IMD 16.

IMD 16 or another component of system 10 may determine a sleep stage of patient 12, using any suitable technique. For example, as described in further detail below, a processor of IMD 16 may determine the sleep stage patient 12 is in based on a frequency characteristic of one or more bioelectrical brain signals of patient 12 sensed via electrodes 22A, 22B of leads 20A and 20B, respectively, or via a separate electrode array that is electrically coupled to IMD 16 or a separate sensing device. In some examples, the bioelectrical brain signal may be detected from external electrodes that are placed on the patient's scalp to sense brain signals.

In addition to determining sleep stages of patient 12, IMD 16 may also determine whether patient 12 experiences one or more seizure events during particular sleep stages. IMD 16 may detect a seizure of patient 12 using any suitable technique. For example, as discussed in further detail below, IMD 16 may detect the onset of a seizure or the possibility of the onset of a seizure based on a bioelectrical brain signal of patient 12. In these examples, the bioelectrical brain signal may be the same as or different than a bioelectrical brain signal used by IMD 16 to determine the sleep stage of patient 12. In some examples, IMD 16 may detect the seizure prior to a physical manifestation of the seizure. In some examples, IMD 16 may detect one or more seizure events of patient 12 based on one or more sensed physiological parameters of patient 12 other than that of bioelectrical brain signals.

In the examples described herein, IMD 16 may detect a seizure of patient 12 using a bioelectrical brain signal sensed by one or more electrodes 22A, 22B implanted within brain 24. However, in other examples, IMD 16 may analyze a different bioelectrical brain signal, such as a bioelectrical brain signal sensed using external electrodes, to detect a seizure event of patient 12. In other examples, IMD 16 may analyze a different physiological parameter or signal, in addition to or instead of a bioelectrical brain signal, to detect a seizure event of patient 12.

IMD 16 may determine that patient 12 is in a particular sleep stage, e.g., REM sleep, during a particular period of time. IMD 16 may also determine the seizure state of patient 12 during the particular period of time. For example, IMD 16 may determine whether or not patient 12 experienced or is experiencing a seizure event at some point during the particular period of time. Based on the seizure state of patient 12 during the particular sleep stage, IMD 16 may subsequently generate a seizure probability metric for the particular sleep stage. As noted above, the seizure probability metric may be indicative of the probability or likelihood that patient 12 will experience a seizure event during the particular sleep stage. In some examples, IMD 16 collects such seizure state data over a period of time during which patient 12 experiences the particular sleep stage multiple different times in order to generate the seizure probability metric for the particular sleep stage, as described in further detail below with respect to FIG. 6. In some examples, IMD 16 may collect seizure state data over an extended period of time, e.g., days, weeks, months, and the like, and generate a seizure probability metric for one or more sleep stages that is cumulative based on all or a portion of the collected data.

In addition, in some examples, IMD 16 may generate multiple seizure probability metrics indicating the probability that patient 12 will experience a seizure event for each of a plurality of sleep stages. IMD 16 may store the multiple seizure probability metrics correlated to a plurality of sleep stages as a seizure probability profile for patient 12. In some examples, a seizure probability profile may allow IMD 16 and/or a clinician to modify treatment parameters, e.g., monitoring and therapy parameters, to more effectively treat a seizure disorder of patient 12 based on patient-specific characteristics of the seizure disorder, namely, the probability that patient 12 may experience a seizure event during a particular sleep stage.

IMD 16 determines one or more seizure probability metrics based on determining sleep stages and corresponding seizure states. As described herein, a seizure state of patient 12 during a particular period of time, e.g., during a particular sleep stage, may be defined by whether or not patient 12 experienced a seizure event at some point during the particular period of time. For example, if patient 12 experienced a seizure event during the particular period of time, patient 12 can be referred to as experiencing a first seizure state during the period of time. Similarly, if patient 12 did not experience a seizure event during the particular period of time, patient 12 can be referred to as experiencing a second seizure state during the period of time. In some examples, IMD 16 may determine the type of seizure a patient experienced during a period of time. For example, IMD 16 may differentiate between simple partial seizures, complex partial seizures, and/or tonic clonic seizures. A seizure probability metric may then be generated to reflect the probability of patient 12 experiencing a particular type of seizure during, e.g., a particular sleep stage.

In some examples, upon detecting a seizure, IMD 16 may deliver therapy to brain 24 of patient 12 to help mitigate the effects of the seizure. In other cases, IMD 16 may deliver therapy to brain 24 of patient 12 to prevent the onset of the seizure. IMD 16 may detect a seizure or the likely onset of a seizure based on bioelectrical brain signals of patient 12. In this way, the bioelectrical brain signals may be used to control therapy delivery to patient 12. IMD 16 may use, for example, a seizure detection algorithm that may include receiving bioelectrical brain signals sensed within brain 24 of patient 12 via, e.g., electrodes 22A, 22B, analyzing the signals, and producing an output that triggers the delivery of therapy or generation of an alert. Examples of systems and methods that include adjusting therapy based on seizure detection algorithms are described in commonly-assigned U.S. Patent Application Publication No. 2010/0121215 by Giftakis, et al., entitled "SEIZURE DETECTION ALGORITHM ADJUSTMENTS," which was filed on Apr. 29, 2009 and is incorporated herein by reference in its entirety.

Additionally or alternatively, rather than delivering therapy to brain 24 of patient 12 in a closed-loop manner, e.g., in response to detecting a seizure, IMD 16 can deliver therapy to patient 12 in an open-loop manner. For example, IMD 16 can deliver therapy to patient 12 on a continuous, substantially continuous, or periodic basis to help mitigate the effects of the seizure or, in some cases, to prevent the onset of the seizure.

In some examples, as discussed in further detail below with respect to FIG. 10, IMD 16 or another component of system 10 may adjust parameters of therapy based on one or more seizure probability metrics generated for one or more particular sleep stages of patient 12. For example, IMD 16 may determine that patient 12 is experiencing a particular sleep stage and may adjust therapy parameters based on the probability that patient 12 will experience a seizure during the particular sleep stage, i.e., based on the seizure probability metric for the particular sleep stage. As an illustration, if IMD 16 determines that patient 12 is experiencing a sleep stage where the seizure probability metric indicates a relatively high likelihood of patient 12 experiencing a seizure, IMD 16 may initiate the delivery of therapy to patient 12 or adjust one or more parameters of therapy being delivered to patient 12 to define a relatively aggressive therapy while patient 12 occupies the particular sleep stage. Conversely, if IMD 16 determines that patient 12 is experiencing a sleep stage where the seizure probability metric indicates a relatively low likelihood of patient 12 experiencing a seizure, IMD 16 may suspend the delivery of therapy to patient 12 or adjust one or more parameters of therapy being delivered to patient 12 to define a relatively nonaggressive therapy while patient 12 occupies the particular sleep stage.

IMD 16 may be implanted within a subcutaneous pocket above the clavicle, or, alternatively, the abdomen, back or buttocks of patient 12, on or within cranium 28 of patient 12, or at any other suitable site within patient 12. Generally, IMD 16 is constructed of a biocompatible material that resists corrosion and degradation from bodily fluids. IMD 16 may comprise a hermetic outer housing or hermetic inner housings within the outer housing to substantially enclose components, such as a processor, therapy module, and memory.

Implanted lead extension 18 is coupled to IMD 16 via connector 30. In the example of FIG. 1, lead extension 18 traverses from the implant site of IMD 16 and along the neck of patient 12 to cranium 32 of patient 12 to access brain 28. Lead extension 18 is electrically and mechanically connected to leads 20A, 20B (collectively "leads 20"). In the example shown in FIG. 1, leads 20 are implanted within the right and left hemispheres, respectively, of patient 12 in order to deliver electrical stimulation to one or more regions of brain 28, which may be selected based on the patient condition or disorder controlled by therapy system 10. Other implant sites for leads 20 and IMD 16 are contemplated. For example, IMD 16 may be implanted on or within cranium 32 or leads 20 may be implanted within the same hemisphere or IMD 16 may be coupled to a single lead.

Although leads 20 are shown in FIG. 1 as being coupled to a common lead extension 18, in other examples, leads 20 may be coupled to IMD 16 via separate lead extensions or directly connected to connector 26 of IMD 16. In addition, in some examples, therapy system 10 may include more than two leads or one lead. While leads 20 and IMD 16 are shown as being implanted, in other example, either or both of leads 20 and IMD 16 may be located externally to patient 12.

Leads 20 may be positioned to sense bioelectrical brain signals within a particular region of brain 24 and to deliver electrical stimulation to one or more target tissue sites within brain 24 to manage patient symptoms associated with a seizure disorder of patient 12. Leads 20 may be implanted to position electrodes 22A, 22B at desired locations of brain 24 through respective holes in cranium 28. For example, electrodes 22A, 22B may be surgically implanted under the dura mater of brain 24 via a burr hole in cranium 28 of patient 12, and electrically coupled to IMD 16 via one or more leads 20. In some examples, IMD 16 may sense and deliver therapy to patient 12 via the same electrodes, while in other examples, IMD 16 may deliver therapy to patient 12 using different electrodes that used to sense bioelectrical brain signals of patient 12.

In the example shown in FIG. 1, electrodes 22A, 22B of leads 20 are shown as ring electrodes. Ring electrodes may be useful in deep brain stimulation applications because they are relatively simple to program and are capable of delivering an electrical field to any tissue adjacent to electrodes 22A, 22B. Similarly, ring electrodes 22A, 22B may be useful in sensing bioelectrical brain signals within brain 24 of patient 12 because they may be capable of sensing the signals in any tissue adjacent to electrodes 22A, 22B, in other examples, electrodes 22A, 22B may have different configurations. For example, in some examples, at least some of the electrodes 22A, 22B of leads 20 have a complex electrode array geometry that is capable of producing shaped electrical fields. The complex electrode array geometry may include multiple electrodes (e.g., partial ring or segmented electrodes) around the outer perimeter of each lead 20, rather than one ring electrode. In this manner, electrical stimulation may be directed to a specific direction from leads 20 to enhance therapy efficacy and reduce possible adverse side effects from stimulating a large volume of tissue. Similarly, a complex electrode array geometry of sensing electrodes 22A, 22B may be capable of sensing changes in bioelectrical brain signals in only a particular portion of brain 24, e.g., the portion of brain 24 proximate to a particular electrode 22A, 22B. In some examples, a housing of IMD 16 includes one or more stimulation and/or sensing electrodes. In alternative examples, leads 20 may have shapes other than elongated cylinders as shown in FIG. 1. For example, leads 20 may be paddle leads, spherical leads, bendable leads, or any other type of shape effective in treating patient 12 and sensing bioelectrical brain signals within brain 24 of patient 12.

In examples in which IMD 16 senses bioelectrical brain signals, e.g., via one or more of electrodes 22A, 22B, IMD 16 may sense the bioelectrical brain signals continuously, e.g., at all times. In other examples, IMD 16 may sense the bioelectrical brain signals intermittently. In some examples, IMD 16 may sense bioelectrical brain signals intermittently during some sleep stages and substantially continuously for other sleep stages based on one or more seizure probability metrics determined for respective sleep stages of patient 12, For example, if IMD 16 determines that patient 12 is experiencing a sleep stage where the seizure probability metric indicates a relatively high likelihood of patient 12 experiencing a seizure, IMD 16 may sense the bioelectrical brain signals of patient 12 on a substantially continuous basis or periodically at a relatively high rate to aggressively monitor for a seizure of patient 12. Conversely, if IMD 16 determines that patient 12 is experiencing a sleep stage where the seizure probability metric indicates a relatively low likelihood of patient 12 experiencing a seizure, IMD 16 may sense the bioelectrical brain signals of patient 12 periodically at a relatively low rate to nonaggressively monitor for a seizure of patient 12.

Electrical stimulation generated by IMD 16 may be configured to manage a variety of disorders and conditions. In some examples, the stimulation generator of IMD 16 is configured to generate and deliver electrical pulses to patient 12 via electrodes of a selected subset of electrodes 22A, 22B (referred to as an "electrode combination"). However, in other examples, the stimulation generator of IMD 16 may be configured to generate and deliver a continuous wave signal, e.g., a sine wave or triangle wave. In either case, a signal generator within IMD 16 may generate the electrical stimulation therapy for DBS according to a therapy program that is selected at that given time in therapy. In examples in which IMD 16 delivers electrical stimulation in the form of stimulation pulses, a therapy program may define values for a set of therapy parameters, such as a stimulation electrode combination for delivering stimulation to patient 12, pulse frequency, pulse width, and a current or voltage amplitude of the pulses. A stimulation electrode combination may indicate the specific electrodes 22A, 22B that are selected to deliver stimulation signals to tissue of patient 12 and the respective polarities of the selected electrodes.

In some examples, IMD 16 includes a memory, which may store a plurality of therapy programs that each defines a set of therapy parameter values. In some examples, IMD 16 may select a therapy program from the memory based on various parameters, such as based on one or more characteristics of a bioelectrical brain signal, based on the time of day, based on a sleep stage of patient 12, based on a seizure probability metric for a particular sleep stage, and the like. IMD 16 may generate electrical stimulation according to the therapy parameter values defined by the selected therapy program to manage the patient symptoms associated with a seizure disorder.

During a trial stage in which IMD 16 is evaluated to determine whether IMD 16 provides efficacious therapy to patient 12, a plurality of therapy programs may be tested and evaluated for efficacy. Therapy programs may be selected for storage within IMD 16 based on the results of the trial stage. During chronic therapy in which IMD 16 is implanted within patient 12 for delivery of therapy on a non-temporary basis, IMD 16 may generate and deliver stimulation signals to patient 12 according to different therapy programs. In addition, in some examples, patient 12 may modify the value of one or more therapy parameter values within a single given program or switch between programs in order to alter the efficacy of the therapy as perceived by patient 12 with the aid of programmer 14. IMD 16 may store instructions defining the extent to which patient 12 may adjust therapy parameters, switch between programs, or undertake other therapy adjustments. Patient 12 may generate additional programs for use by IMD 16 via external programmer 14 at any time during therapy or as designated by the clinician.

External programmer 14 wirelessly communicates with IMD 16 to retrieve information related to data sensed by electrodes 22A, 22B or other components of therapy system 10. Additionally, external programmer 14 may wirelessly communicate with IMD 16 to provide or retrieve information related to delivery of therapy to patient 12. Programmer 14 is an external computing device that a user, e.g., a clinician and/or patient 12, may use to communicate with IMD 16. For example, programmer 14 may be a clinician programmer that a clinician uses to communicate with IMD 16 in order to program one or more therapy programs for IMD 16. Alternatively, programmer 14 may be a patient programmer that allows patient 12 to select programs and/or view and modify therapy parameters. In some examples, the clinician programmer may include more programming features than the patient programmer. In other words, in some examples, more complex or sensitive tasks may only be allowed by the clinician programmer to prevent an untrained patient from making undesired changes to IMD 16.

In some examples, IMD 16 may transmit information to programmer 14 regarding seizure probability metrics for one or more particular sleep stages of patient 12. For example, IMD 16 may transmit particular seizure probability metrics correlating to particular sleep stages of patient 12 to programmer 14 such that a user, e.g., patient 12 or a clinician, may access the seizure probability metrics. In this way, patient 12 or a clinician may modify treatment parameters, e.g., monitoring and/or therapy parameters, based on the seizure probability metrics. In some examples, a memory of programmer 14 may store the seizure probability metrics, e.g., in the form of a seizure probability profile, for patient 12.

Programmer 14 may be a handheld computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate through the user interface of programmer 14 and provide input. If programmer 14 includes buttons and a keypad, the buttons may be dedicated to performing a certain function (e.g., a power button) or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or a finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20, the arrangement of electrodes 22A, 22B on leads 20, the position of leads 20 within brain 24, the configuration of electrode array 22A, 22B, initial programs defining therapy parameter values, and any other information the clinician desires to program into IMD 16. Programmer 14 may also be capable of completing functional tests (e.g., measuring the impedance of electrodes 22A, 22B of leads 20).

The clinician may also store therapy programs within IMD 16 with the aid of programmer 14. During a programming session, the clinician may determine one or more therapy programs that provide efficacious therapy to patient 12 to address symptoms associated with the seizure disorder. For example, the clinician may select one or more electrode combinations with which stimulation is delivered to brain 24. During the programming session, patient 12 may provide feedback to the clinician as to the efficacy of the specific program being evaluated or the clinician may evaluate the efficacy based on one or more physiological parameters of patient (e.g., heart rate, respiratory rate, or muscle activity). Programmer 14 may assist the clinician in the creation/identification of therapy programs by providing a methodical system for identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Programmer 14 may also provide an indication to patient 12 when therapy is being delivered, when patient input has triggered a change in therapy or when the power source within programmer 14 or IMD 16 needs to be replaced or recharged. For example, programmer 14 may include an alert LED, may flash a message to patient 12 via a programmer display, generate an audible sound or somatosensory cue to confirm patient input was received, e.g., to indicate a patient state or to manually modify a therapy parameter. In addition, in examples in which IMD 16 or programmer 14 can automatically detect a seizure, e.g., using a seizure detection algorithm, programmer 14 may provide a notification to patient 12, a caregiver, and/or a clinician when a seizure is detected by IMD 16. A notification of a likelihood of a seizure may provide patient 12 with sufficient notice to, for example, prepare for the onset of the seizure (e.g., by stopping a vehicle if patient 12 is driving the vehicle).

Programmer 14 is configured to communicate with IMD 16 and, optionally, another computing device, via wireless communication. For example, IMD 16 may generate and wirelessly transmit signals to programmer 14 for display on the user interface of programmer 14. Programmer 14 may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth® specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

In some examples, therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively tong-term treatment.

In addition to or instead of electrical stimulation therapy, IMD 16 may deliver a therapeutic agent to patient 12 to manage a seizure disorder. In such examples, IMD 16 may include a fluid pump or another device that delivers a therapeutic agent in some metered or other desired flow dosage to the therapy site within patient 12 from a reservoir within IMD 16 via a catheter. IMD 16 may deliver the therapeutic agent upon detecting a seizure with a seizure detection algorithm that detects the seizure based on bioelectrical brain signals or another patient parameter. The catheter used to deliver the therapeutic agent to patient 12 may include one or more electrodes for sensing bioelectrical brain signals of patient 12.

Examples of therapeutic agents that IMD 16 may deliver to patient 12 to manage a seizure disorder include, but are not limited to, lorazepam, carbamazepine, oxcarbazepine, valproate, divalproex sodium, acetazolamide, diazepam, phenytoin, phenytoin sodium, felbamate, tiagabine, levetiracetam, clonazepam, lamotrigine, primidone, gabapentin, phenobarbital, topiramate, clorazepate, ethosuximide, and zonisamide. Other therapeutic agents may also provide effective therapy to manage the patient's seizure disorder, e.g., by minimizing the severity, duration, and/or frequency of the patient's seizures. In other examples, IMD 16 may deliver a therapeutic agent to tissue sites within patient 12 other than brain 24.

Figure 2:
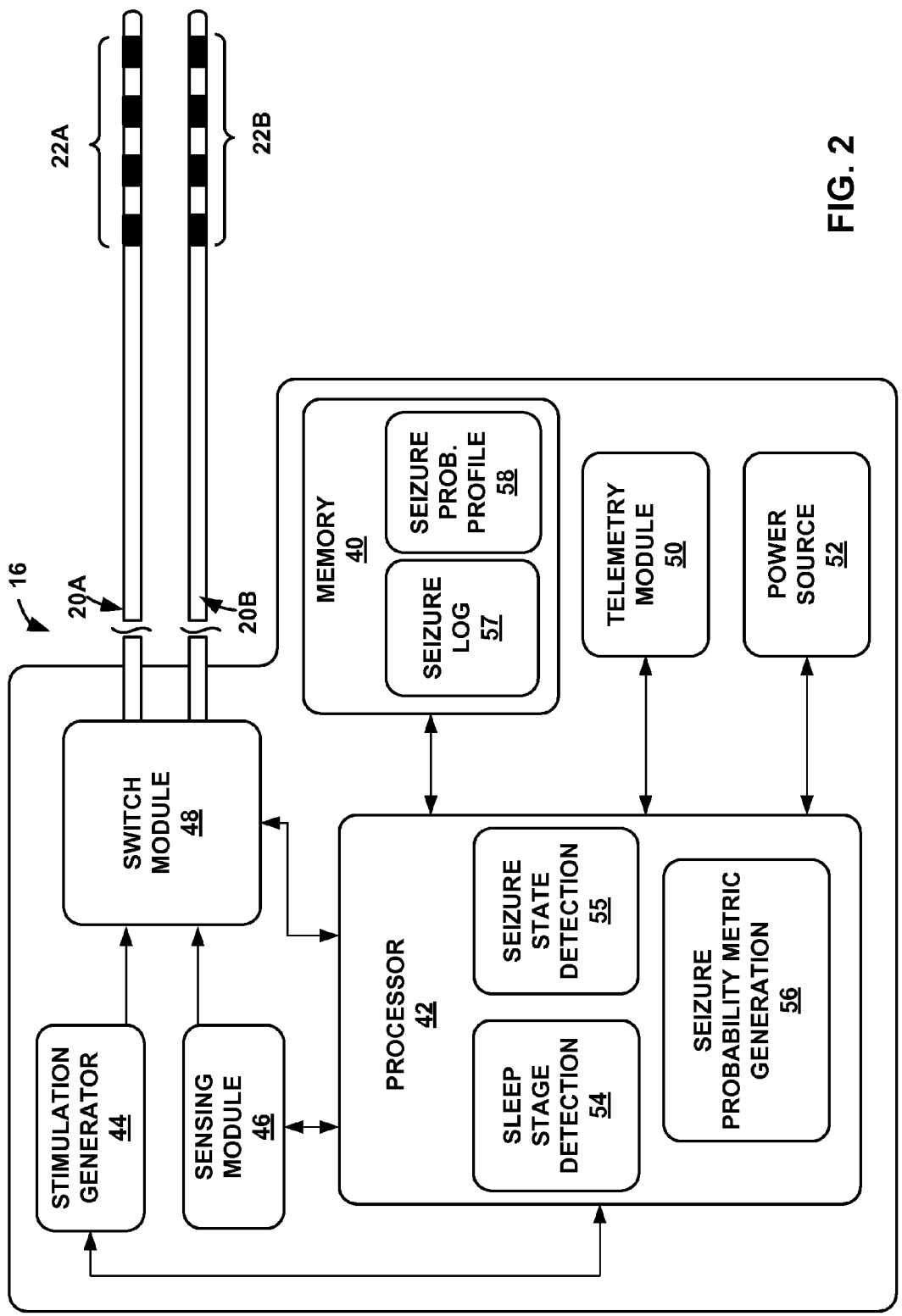
FIG. 2 is a functional block diagram illustrating example components of an example medical device.

FIG. 2 is a functional block diagram illustrating components of an example IMD 16. In the example shown in FIG. 2, IMD 16 includes memory 40, processor 42, stimulation generator 44, sensing module 46, switch module 48, telemetry module 50, and power source 52. Processor 42 includes sleep stage detection module 54, seizure state detection module 55, and seizure probability metric generation module 56. Memory 40 includes seizure log module 57 and seizure probability profile module 58. Processor 42 may include any one or more microprocessors, controllers, digital signal processors (DSPs), application specific integrated circuits (ASICs), field-programmable gate arrays (FPGAs), and discrete logic circuitry. The functions attributed to processors described herein, including processor 42, may be provided by a hardware device and embodied as software, firmware, hardware, or any combination thereof.

Processor 42 may utilize any suitable type of signal or input to determine sleep stages and seizure states of patient 12. In the examples described herein, sensing module 46 senses bioelectrical brain signals via one or more of electrodes 22A, 22B, which processor 42 utilizes to detect sleep stages of patient 12 and seizure states of patient 12. However, in other examples, processor 42 may utilize different types of signals or input to determine sleep stages and/or seizure states of patient 12. For example, processor 42 may utilize parameters such as intracranial pressure or signals indicative of patient movement or posture state (e.g., using one or more accelerometer sensors), instead of or in addition to a bioelectrical brain signal, to determine a seizure state of patient 12.

In the example shown in FIG. 2, sensing module 46 senses bioelectrical brain signals of patient 12 via select combinations of electrodes 22A, 22B. Sensing module 46 may include circuitry that measures the electrical activity of a particular region, e.g., an anterior nucleus (AN), thalamus or cortex of brain 24 via select electrodes 22A, 22B. Sensing module 46 may acquire the bioelectrical brain signal substantially continuously or at regular intervals, such as, but not limited to, a frequency of about 1 Hz to about 1000 Hz, such as about 250 Hz to about 1000 Hz or about 500 Hz to about 1000 Hz. Sensing module 46 includes circuitry for determining a voltage difference between two electrodes 22A, 22B, which generally indicates the electrical activity within the particular region of brain 24. One of the electrodes 22A, 22B may act as a reference electrode, and, if sensing module 46 is implanted within patient 12, a housing of IMD 16 or the sensing module in examples in which sensing module 46 is separate from IMD 16, may include one or more electrodes that may be used to sense bioelectrical brain signals.

The output of sensing module 46 may be received by processor 42. In some cases, processor 42 may apply additional processing to the bioelectrical signals, e.g., convert the output to digital values for processing and/or amplify the bioelectrical brain signal. In addition, in some examples, sensing module 46 or processor 42 may filter the signal from the selected electrodes 22A, 22B in order to remove undesirable artifacts from the signal, such as noise from electrocardiogram signals generated within the body of patient 12. Although sensing module 46 is incorporated into a common outer housing with stimulation generator 44 and processor 42 in FIG. 2, in other examples, sensing module 46 is in a separate outer housing from the outer housing of IMD 16 and communicates with processor 42 via wired or wireless communication techniques. In other examples, a bioelectrical brain signal may be sensed via external electrodes (e.g., scalp electrodes).

In the example illustrated in FIG. 2, sleep stage detection module 54 of processor 42 determines that patient 12 is in a particular sleep stage based on a bioelectrical brain signal received from sensing module 46. However, sleep stage detection module 54 may employ any suitable technique to determine a sleep stage of patient 12.

In some examples, sleep stage detection module 54 may determine the sleep stage of patient 12 based on a frequency characteristic of one or more bioelectrical brain signals sensed by sensing module 46. For example, sleep stage detection module 54 may analyze a bioelectrical brain signal sensed via one or more of electrodes 22A, 22B to determine a sleep stage of patient 12 using a frequency characteristic of the bioelectrical brain signal (e.g., a power level or energy within one or more frequency bands of the bioelectrical brain signal, a ratio of the power level in two or more frequency bands, a correlation in change of power between two or more frequency bands, a pattern in the power level of one or more frequency bands over time, and the like). In some examples, sleep stage detection module 54 may analyze the bioelectrical brain signal in the frequency domain by comparing selected frequency components of an amplitude waveform of the bioelectrical brain signal to corresponding frequency components of a template signal or a threshold value, e.g., by performing a spectral analysis of the signal. If sleep stage detection module 54 determines that the bioelectrical brain signal exhibits frequency components similar to those of the template signal or threshold value for a particular sleep stage, sleep stage detection module 54 may determine that patient 12 is experiencing the particular sleep stage.

Sleep stage detection module 54 may utilize these and other techniques described in U.S. Patent Application Publication No. 2009/0192556 by Wu et al., entitled "SLEEP STAGE DETECTION," which is incorporated herein by reference in its entirety, to determine a sleep stage of patient 12. In some examples described herein, sleep stage detection module 54 determines whether patient 12 is in one of a Stage 1 sleep stage, a Stage 2 sleep stage, a Deep Sleep stage (which may include Stage 3 and Stage 4 sleep stages), a REM sleep stage, or an awake stage.

In some examples, sleep stage detection module 54 may monitor one or more physiological parameters of a patient which are indicative of the patient sleep stage to determine the sleep stage of patient 12, e.g., in combination with the monitored bioelectrical brains signals of the patients. Suitable patient physiological parameters may include, but are not limited to, muscle tone (e.g., as sensed via electromyography (EMG)), eye movement (e.g., as sensed via electroculography (EOG) or EEG), and body temperature. In some examples, patient movement may be monitored via actigraphy. In one example, sleep stage detection module 54 may monitor an EMG signal reflective of the muscle tone of patient 12 to identify physical movement of the patient, and determine the sleep stage of patient 12. Alternatively or additionally, sleep stage detection module 54 may monitor the physical movement of a patient via one or more motion sensors, such as, e.g., one or more single or multi-axis accelerometer devices, and determine the sleep stage of patient 12 based on the physical movement of patient 12.

In addition, seizure state detection module 55 may determine a seizure state of patient 12 during a particular sleep stage. For example, sleep stage detection module 54 may determine that patient 12 experienced a particular sleep stage during a particular period of time based on a first portion of a bioelectrical brain signal indicative of electrical activity in brain 24 of patient 12 during the particular period of time. Seizure state detection module 55 may analyze the first portion of the same bioelectrical brain signal or a portion of another signal temporally correlated to the first portion of the bioelectrical brain signal to determine the seizure state of patient 12, e.g., to determine whether patient 12 experienced a seizure event, during the particular period of time in which patient 12 experienced the particular sleep stage. In this way, seizure state detection module 55 may determine a seizure state of patient 12 during a particular sleep stage.

Seizure state detection module 55 can determine a seizure state of patient 12 using any suitable technique to determine whether patient 12 experienced a seizure during a sleep stage. Examples of detecting bioelectrical brain signal characteristics indicative of a seizure are described in U.S. Pat. No. 7,006,872 to Gielen et al., entitled, "CLOSED LOOP NEUROMODULATION FOR SUPPRESSION OF EPILEPTIC ACTIVITY," which issued on Feb. 28, 2006, U.S. Pat. No. 7,006,872 to Gielen et al. is incorporated herein by reference in its entirety. As described in U.S. Pat. No. 7,006,872 to Gielen et al., EEG data may be analyzed and a seizure detected when the EEG data exhibits one or more characteristics previously determined to be indicative an onset of a seizure.

In some examples, seizure state detection module 55 detects a seizure by comparing an amplitude of a sensed bioelectrical brain signal to a threshold value that is stored as part of the seizure detection algorithm in memory 40. The amplitude may be an instantaneous, average, median, lowest or highest amplitude over a predetermined range of time. In one example, when the amplitude of the bioelectrical signal is greater than or equal to the threshold value, seizure state detection module 55 detects a seizure. In some examples, processor 42 may control stimulation generator 44 to generate and deliver therapy to patient 12 via selected electrodes 22A, 22B to treat the detected seizure.

In other examples, seizure state detection module 55 may detect a seizure by comparing a slope of the time domain bioelectrical brain signal over time or timing between inflection points or other critical points in the pattern of the amplitude of the bioelectrical brain signal over time to trend information. The trend information may be stored as part of the seizure detection algorithm in memory 40. A substantial correlation (e.g., 75% or greater correlation) between the inflection points in the amplitude waveform of the bioelectrical brain signal or other critical points and a template may indicate the onset or a likely onset of a seizure. Seizure state detection module 55 may store an algorithm that recognizes a trend of the bioelectrical brain signal that characterizes a brain state that indicates the onset or the potential onset of the seizure. If the trend of the bioelectrical brain signal matches or substantially matches the trend template, seizure state detection module 55 detects a seizure. In some examples, processor 42 may control stimulation generator 44 to generate and deliver therapy to patient 12 via selected electrodes 22A, 22B to treat the detected seizure.

As another example, seizure state detection module 55 may perform temporal correlation by sampling the bioelectrical brain signal with a sliding window and comparing the sampled waveform with a stored template waveform. For example, seizure state detection module 55 may perform a correlation analysis by moving a window along a digitized plot of the amplitude waveform of bioelectrical brain signal at regular intervals, such as between about one millisecond to about ten millisecond intervals, to define a sample of the bioelectrical brain signal. The sample window is slid along the plot until a correlation is detected between the waveform of the template and the waveform of the sample of the bioelectrical brain signal defined by the window. By moving the window at regular time intervals, multiple sample periods are defined. The correlation may be detected by, for example, matching multiple points between the template waveform and the waveform of the plot of the bioelectrical brain signal over time, or by applying any suitable mathematical correlation algorithm between the sample in the sampling window and a corresponding set of samples stored in the template waveform.

In some examples, seizure state detection module 55 detects a seizure based on one or more frequency domain characteristics of a bioelectrical brain signal. Either sensing module 46 or seizure state detection module 55 may tune the bioelectrical brain signal to a particular frequency band that is indicative of the patient's seizure state. The power level within the selected frequency band may be indicative of whether the bioelectrical brain signal indicates patient 12 is in a seizure state. In another example, the ratio of power levels within two or more frequency bands may be compared to a stored value in order to determine whether the bioelectrical brain signal indicates patient 12 is in a seizure state. In another example, the correlation of changes of power between frequency bands may be compared to a stored template to determine whether the bioelectrical brain signal indicates patient 12 is in a seizure state. Thus, in some cases, the algorithm with which seizure state detection module 55 detects a seizure based on the frequency band characteristics may include a power level within a selected frequency band that is indicative of the seizure state, a ratio of power levels within two or more frequency bands that is indicative of the seizure state, and a relationship between changes in power in two or more frequency bands over time that is indicative of the seizure state.

Another example of a seizure detection algorithm that seizure state detection module 55 may implement to detect a seizure is described in commonly-assigned U.S. Patent Application Publication No. 2008/0269631 by Denison et al., which is entitled, "SEIZURE PREDICTION" and was filed on Apr. 30, 2007. U.S. Patent Application Publication No. 2008/0269631 by Denison et al. is incorporated herein by reference in its entirety. According to some example techniques disclosed by U.S. Patent Application Publication No. 2008/0269631 by Denison et al., seizure state detection module 55 may detect a seizure event based on impedance of tissue within brain 24, which may be sensed via any suitable combination of electrodes 22A, 22B. For example, as described in U.S. Patent Application Publication No. 2008/0269631 by Denison et al., an impedance of brain 24 of patient 12 may be measured by delivering a stimulation current to brain 24 via implanted electrodes. The stimulation current may be relatively low to prevent inadvertent stimulation of tissue and to prevent patient 12 from feeling the stimulation current. For example, the stimulation current may be in a range of about 500 nanoamps (nA) to about 10 microamps (µA), although other stimulation currents may be used.

Alternatively or additionally, seizure state detection module 55 may utilize other suitable techniques to detect a seizure of patient 12. For example, seizure state detection module 55 may receive one or more signals indicative of patient activity, e.g., from one or more accelerometer sensors positioned on or implanted within patient 12, and may determine that patient 12 has experienced or will experience a seizure event based on particular patient postures or changes in patient postures discerned from the one or more signals indicative of patient motion. In some examples, patient activity may also be detected via one or more EMG sensors that generate an electrical signal indicative of muscle movement or one or more intracranial pressure sensors that indicate a change in pressure in cranium 28, which may result from changes in patient posture or a change in patient activity level. Commonly-assigned U.S. Patent Application Publication No. 2010/0121213 by Giftakis et al., which is entitled, "SEIZURE DISORDER EVALUATION BASED ON INTRACRANIAL PRESSURE AND PATIENT MOTION" and was filed on Jan. 23, 2009, and U.S. Patent Application Publication No. 2010/0121214 by Giftakis et al., which is entitled, "SEIZURE DISORDER EVALUATION BASED ON INTRACRANIAL PRESSURE AND PATIENT MOTION" and was filed on Jan. 23, 2009 describe ways in which intracranial pressure information may be useful for detecting patient posture transitions. U.S. Patent Application Publication Nos. 2010/0121213 and 2010/0121214 are incorporated herein by reference in their entireties.

In examples in which IMD 16 determines the sleep stage and seizure state of patient 12 based on sensed bioelectrical brain signals, the same or different electrodes may be used to sense the brain signals for the determination. In each case, such electrodes may be the same or different from the electrodes used by IMD 16 to deliver electrical stimulation to the brain of patient 12. In some examples, sleep stage detection module 54 may utilize signals (e.g., LFP signals) sensed from electrodes on existing therapy leads, e.g., electrodes 22A, 22B when used to deliver therapy to the brain of patient 12. Additionally or alternatively, sleep state detection module 54 may utilize signals (e.g., LFP signals) sensed from electrodes positioned to monitor for sleep stage and sleep stage transitions (e.g., in the frontal cortex) which may not be used to deliver therapy to patient 12. Additionally or alternatively, sleep state detection module 54 may utilize signals (e.g., LFP signals) sensed from external electrodes positioned to monitor for sleep stage and sleep stage transitions using EEG electrode signals.

Based on the seizure state of patient 12 during particular sleep stages, seizure probability metric generation module 56 may generate one or more seizure probability metrics for the particular sleep stages. The seizure probability metrics may be any metrics indicative of the susceptibility of patient 12 to seizure events during a particular sleep stage, e.g., indicative of the likelihood or probability that patient 12 will experience a seizure event during the particular sleep stage. For example, the seizure probability metrics may be a numerical percentage value that indicates a percentage chance that patient 12 will experience a seizure event during a particular sleep stage based on sleep stage data and seizure state data previously detected. A seizure probability metric generated for a sleep stage may generally reflect the absolute probability of patient 12 experiencing a seizure during the respective sleep stage and/or may generally reflect the probability of patient 12 experiencing a seizure during the respective sleep stage relative to one more other sleep stages.

In some examples, a seizure probability metric generated for a sleep stage may be based on the frequency at which a patient has experienced a seizure while occupying the particular sleep stage. The frequency may be expressed in terms of number of times a seizure has been experienced per the number of times the patient has occupied the particular sleep stage. Additionally or alternatively, the frequency may be expressed in terms of number of times a seizure has been experienced per the total amount of time spent in the particular seizure state. Additionally or alternatively, a seizure state probability metric may be based on the total amount of time the patient has experienced a seizure per the total amount of time spent in the particular seizure state. In each case, the seizure state during the particular sleep stage may be whether or not patient 12 experienced any type of seizure, and/or may be based on the particular type of seizure (e.g., simple partial seizure, complex partial seizure, and/or tonic clonic seizure).

As discussed in further detail below with respect to FIG. 6, in some examples, processor 42 may collect seizure state data for a particular sleep stage over a time period in which patient 12 occupies the particular sleep stage multiple different times in order to generate a seizure probability metric for the particular sleep stage. In some examples, a seizure probability metric for a particular sleep stage may be substantially more likely to accurately reflect susceptibility of patient 12 to a seizure event if seizure probability metric generation module 56 generates the seizure probability metric for the particular sleep stage based on seizure state data collected over such a time period, instead of based on seizure state data collected during only a period of time in which patient 12 occupied the particular sleep stage just once.

In order to collect seizure state data for a particular sleep stage over a time period during which patient 12 occupies the particular sleep stage multiple different times, in some examples, processor 42 may store seizure state data for the particular sleep stage within seizure log 57 of memory 40. For example, sleep stage detection module 54 may determine that, during the time period in question, patient 12 experienced a particular sleep stage multiple times. For each detected occurrence of the particular sleep stage, seizure state detection module 55 may determine the corresponding seizure state of patient 12 during the particular sleep stage, and may subsequently store an indication of each of the seizure states of patient 12 during the particular sleep stage in seizure log 57. When seizure log 57 contains sufficient data to generate a seizure probability metric for the particular sleep stage, seizure probability metric generation module 56 may generate the seizure probability metric for the particular sleep stage based on the seizure state data for the respective time period stored in seizure log 57. Even after seizure probability metric generation module 56 generates a seizure probability metric for the particular sleep stage, seizure probability metric generation module 56 may dynamically update the seizure probability metric for the particular sleep stage based on the seizure state of patient 12 during one or more future occurrences of patient 12 experiencing the particular sleep stage.

In some examples, IMD 16 may create a seizure probability profile for patient 12, which can include a plurality of seizure probability metrics, each of which may correspond to a particular sleep stage experienced by patient 12. For example, seizure log 57 may include a plurality of seizure logs, each of which corresponds to a respective sleep stage experienced by patient 12. When each of the plurality of seizure logs within seizure log 57 includes sufficient seizure state data for a respective sleep stage, seizure probability metric generation module 56 may generate a seizure probability metric for each of the sleep stages. Seizure probability metric generation module 56 may store each the respective seizure probability metrics corresponding to its respective sleep stage within seizure probability profile 58 to create a seizure probability profile for patient 12. In some examples, processor 42 or a user may access the seizure probability profile to modify treatment parameters during particular sleep stages, e.g., sleep stages in which patient 12 may be more or less susceptible to experiencing a seizure event, to more effectively treat the seizure disorder of patient 12.

Memory 40 may include any volatile or non-volatile media, such as a random access memory (RAM), read only memory (ROM), non-volatile RAM (NVRAM), electrically erasable programmable ROM (EEPROM), flash memory, and the like. Memory 40 may store computer-readable instructions that, when executed by processor 42, cause IMD 16 to perform various functions described herein. In the example shown in FIG. 2, memory 40 stores seizure log data 57 and seizure probability profile data 58 in separate memories within memory 40 or separate areas within memory 40.

Memory 40 may be considered, in some examples, a non-transitory computer-readable storage medium comprising instructions that cause one or more processors, such as, e.g., processor 42, to implement one or more of the example techniques described in this disclosure. The term "non-transitory" may indicate that the storage medium is not embodied in a carrier wave or a propagated signal. However, the term "non-transitory" should not be interpreted to mean that memory 40 is non-movable. As one example, memory 40 may be removed from IMD 16, and moved to another device. In certain examples, a non-transitory storage medium may store data that can, over time, change (e.g., in RAM).

In the example shown in FIG. 2, the set of electrodes 22A of lead 20A includes four electrodes, and the set of electrodes 22B of lead 20B includes four electrodes. Processor 42 controls switch module 48 to sense bioelectrical brain signals with selected combinations of electrodes 22A, 22B. In particular, switch module 48 may create or cut off electrical connections between sensing module 46 and selected electrodes 22A, 22B in order to selectively sense bioelectrical brain signals, e.g., in particular portions of brain 24 of patient 12. Processor 42 may also control switch module 48 to apply stimulation signals generated by stimulation generator 44 to selected combinations of electrodes 22A, 22B. In particular, switch module 48 may couple stimulation signals to selected conductors within leads 20, which, in turn, deliver the stimulation signals across selected electrodes 22A, 22B. Switch module 48 may be a switch array, switch matrix, multiplexer, or any other type of switching module configured to selectively couple stimulation energy to selected electrodes 22A, 22B and to selectively sense bioelectrical brain signals with selected electrodes 22A, 22B. Hence, stimulation generator 44 is coupled to electrodes 22A, 22B via switch module 48 and conductors within leads 20. In some examples, however, IMD 16 does not include switch module 48.

Stimulation generator 44 may be a single channel or multi-channel stimulation generator. For example, stimulation generator 44 may be capable of delivering, a single stimulation pulse, multiple stimulation pulses or a continuous signal at a given time via a single electrode combination or multiple stimulation pulses at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12.

Telemetry module 50 may support wireless communication between IMD 16 and an external programmer 14 or another computing device under the control of processor 42. Processor 42 of IMD 16 may, for example, transmit bioelectrical brain signals, seizure probability metrics for particular sleep stages, a seizure probability profile for patient 12, and the like via telemetry module 50 to a telemetry module within programmer 14 or another external device. Telemetry module 50 in IMD 16, as well as telemetry modules in other devices and systems described herein, such as programmer 14, may accomplish communication by radiofrequency (RF) communication techniques. In addition, telemetry module 50 may communicate with external programmer 14 via proximal inductive interaction of IMD 16 with programmer 14. Accordingly, telemetry module 50 may send information to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
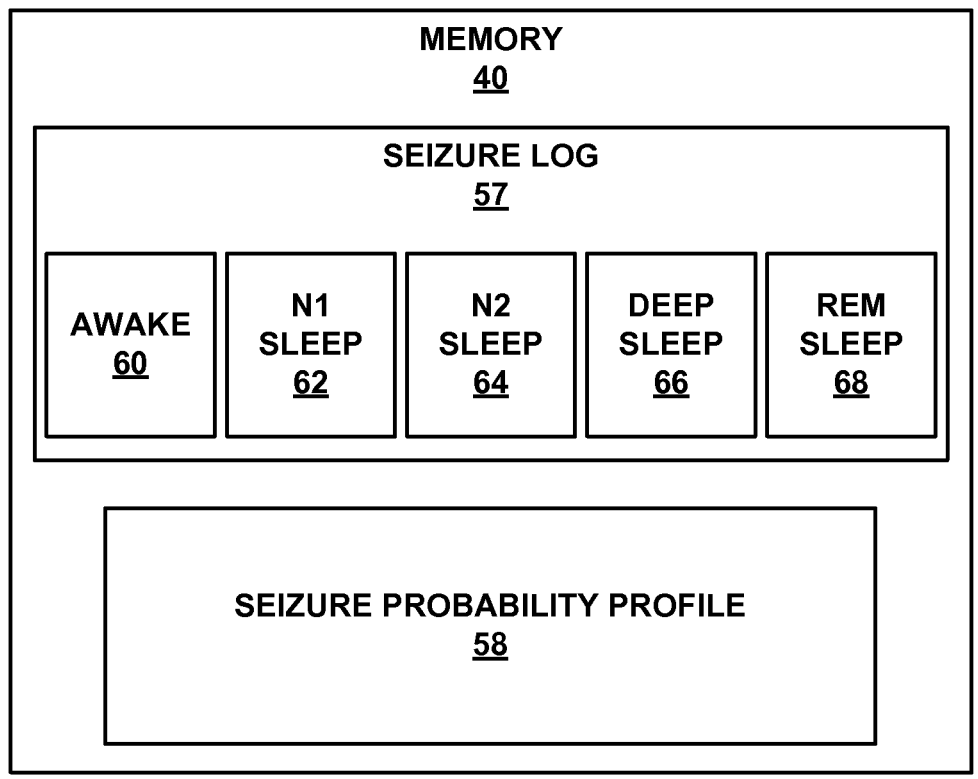
FIG. 3 is a functional block diagram illustrating example storage modules of the memory of the example medical device of FIG. 2.

FIG. 3 illustrates an example configuration of memory 40 (FIG. 2). In the example illustrated in FIG. 3, seizure log 57 includes awake module 60, N1 sleep module 62, N2 sleep module 64, Deep Sleep module 66, and REM sleep module 68, which correspond to multiple different sleep stages that may be experienced by patient 12 over a given period of time. In other examples, seizure log 57 may include additional or alternative modules corresponding to additional or alternative sleep stages that may be experienced by patient 12.

As discussed above with respect to FIG. 2, in some examples, seizure state detection module 55 may store seizure state data for a time period in which patient 12 experienced a particular sleep stage multiple different times in seizure log 57 of memory 40 and, in addition, may do so for multiple different sleep stages. For example, with respect to FIG. 3, seizure state detection module 55 may store seizure data for a time period in which patient 12 experienced an awake stage multiple different times, a time periods in which patient 12 experienced N1 sleep stage multiple different times, a time period in which patient 12 experienced N2 sleep stage multiple different times, a time periods in which patient 12 experienced Deep Sleep stage multiple different times, and/or a time periods in which patient 12 experienced REM sleep stage multiple different times, and store the seizure data in awake module 60, N1 sleep module 62, N2 sleep module 64, Deep Sleep module 66, and REM sleep module 68, respectively. Seizure data stored in seizure log 70 for a particular sleep stage may include information indicating the number of times patient 12 has experienced the sleep stage, the number of times patient 12 experienced a seizure during the sleep stage, the number of times the onset of a seizure was predicted (whether or not therapy was delivered to prevent the seizure), and/or the number of times patient 12 did not experience a seizure during the sleep stage.

Seizure probability metric generation module 56 may subsequently generate a seizure probability metric for each of the awake stage, the N1 sleep stage, the N2 sleep stage, the Deep Sleep stage, and the REM sleep stage for patient 12 based on the seizure data stored in modules 60, 62, 64, 66, and 68, respectively. In some examples, processor 42 may store the plurality of seizure probability metrics corresponding to sleep stages in seizure probability profile 58 as a seizure probability profile for patient 12 such that a component of therapy system 10 and/or a user may access the seizure probability metrics to increase efficacy of monitoring and therapy to treat the seizure disorder of patient 12.

Figure 4:
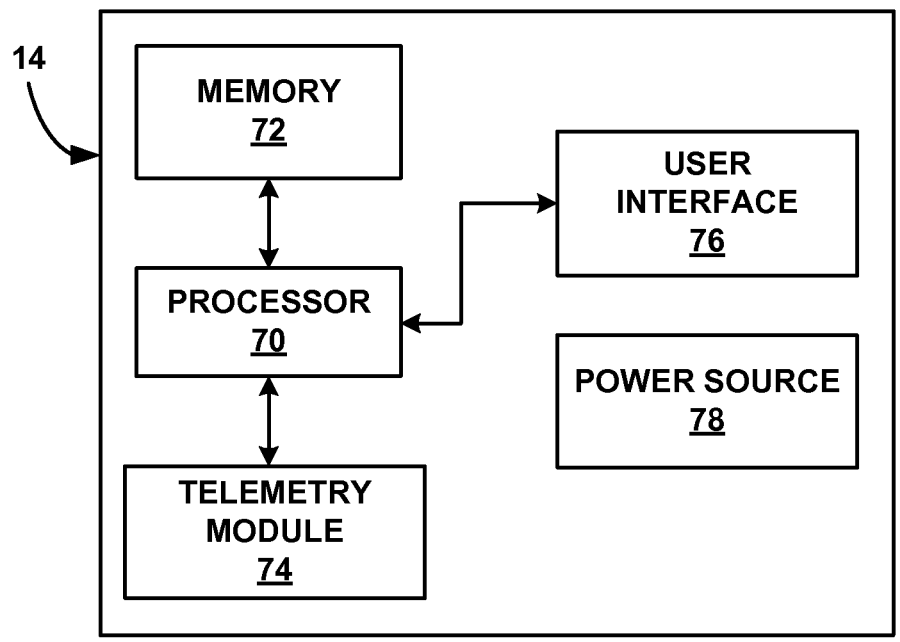
FIG. 4 is a functional block diagram illustrating example components of an example medical device programmer.

FIG. 4 is a conceptual block diagram of an example external medical device programmer 14, which includes processor 70, memory 72, telemetry module 74, user interface 76, and power source 78. Processor 70 controls user interface 76 and telemetry module 74, and stores and retrieves information and instructions to and from memory 72. Programmer 14 may be configured for use as a clinician programmer or a patient programmer. Processor 70 may comprise any combination of one or more processors including one or more microprocessors, DSPs, ASICs, FPGAs, or other equivalent integrated or discrete logic circuitry. Accordingly, processor 70 may include any suitable structure, whether in hardware, software, firmware, or any combination thereof, to perform the functions ascribed herein to processor 70.

A user, such as a clinician or patient 12, may interact with programmer 14 through user interface 76. User interface 76 includes a display (not shown), such as a LCD or LED display or other type of screen, to present information related to treatment of the seizure disorder of patient 12. For example, user interface 76 may display bioelectrical brain signal data sensed via a plurality of sense electrode combinations, sleep stage data, seizure state data, seizure probability metrics for particular sleep stages of patient 12, or a seizure probability profile for patient 12. In some examples, the display may be used to present a visual alert to patient 12 that IMD 16 has detected a seizure is about to occur. Other types of alerts are contemplated, such as audible alerts or somatosensory alerts. User interface 76 may also include an input mechanism to receive input from the user. The input mechanisms may include, for example, buttons, a keypad (e.g., an alphanumeric keypad), a peripheral pointing device or another input mechanism that allows the user to navigate through user interfaces presented by processor 70 of programmer 14 and provide input.

If programmer 14 includes buttons and a keypad, the buttons may be dedicated to performing a certain function, i.e., a power button, or the buttons and the keypad may be soft keys that change function depending upon the section of the user interface currently viewed by the user. Alternatively, the screen (not shown) of programmer 14 may be a touch screen that allows the user to provide input directly to the user interface shown on the display. The user may use a stylus or their finger to provide input to the display. In other examples, user interface 76 also includes audio circuitry for providing audible instructions or notifications to patient 12 and/or receiving voice commands from patient 12, which may be useful if patient 12 has limited motor functions. Patient 12, a clinician or another user may also interact with programmer 14 to manually select therapy programs, generate new therapy programs, modify therapy programs through individual or global adjustments, and transmit the new programs to IMD 16.

In some examples, at least some control of treatment of patient 12 may be implemented by processor 70. For example, in some examples, processor 70 may receive sleep stage information, seizure state information, or seizure probability information (e.g., seizure probability metrics or a seizure probability profile) from IMD 16 or from another component of therapy system 10. In some examples, processor 70 may evaluate the information and modify treatment parameters based on the information. For example, processor 70 may modify sleep stage detection parameters, seizure state detection parameters (e.g., parameters of a seizure detection algorithm), or therapy parameters based on the information. Additionally or alternatively, a clinician may provide input to programmer 14, e.g., via user interface 76, to modify treatment parameters based on the information, e.g., based on viewing the information via user interface 76.

Memory 62 may include instructions for operating user interface 76 and telemetry module 74, and for managing power source 78. Memory 72 may also store any therapy data retrieved from IMD 16 during the course of therapy, as well as seizure data (e.g., seizure indications that indicate the time and date of a seizure), sensed bioelectrical brain signals, and sleep stage information. The clinician may use this therapy data to determine the progression of the patient condition in order to plan future treatment for the seizure disorder of patient 12. Memory 72 may include any volatile or nonvolatile memory, such as RAM, ROM, EEPROM or flash memory. Memory 72 may also include a removable memory portion that may be used to provide memory updates or increases in memory capacities. A removable memory may also allow sensitive patient data to be removed before programmer 14 is used by a different patient.

Memory 62 may be considered, in some examples, a non-transitory computer-readable storage medium comprising instructions that cause one or more processors, such as, e.g., processor 70, to implement one or more of the example techniques described in this disclosure. The term "non-transitory" may indicate that the storage medium is not embodied in a carrier wave or a propagated signal. However, the term "non-transitory" should not be interpreted to mean that memory 62 is non-movable. As one example, memory 62 may be removed from programmer 14, and moved to another device. In certain examples, a non-transitory storage medium may store data that can, over time, change (e.g., in RAM).

Wireless telemetry in programmer 14 may be accomplished by RF communication or proximal inductive interaction of external programmer 14 with IMD 16. This wireless communication is possible through the use of telemetry module 74. Accordingly, telemetry module 74 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 78 may deliver operating power to the components of programmer 14. Power source 78 may include a battery and a power generation circuit to produce the operating power. In some examples, the battery may be rechargeable to allow extended operation. Recharging may be accomplished by electrically coupling power source 78 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to obtain operating power. Power source 78 may include circuitry to monitor power remaining within a battery. In this manner, user interface 76 may provide a current battery level indicator or low battery level indicator when the battery needs to be replaced or recharged. In some cases, power source 78 may be capable of estimating the remaining time of operation using the current battery.

Figure 5:
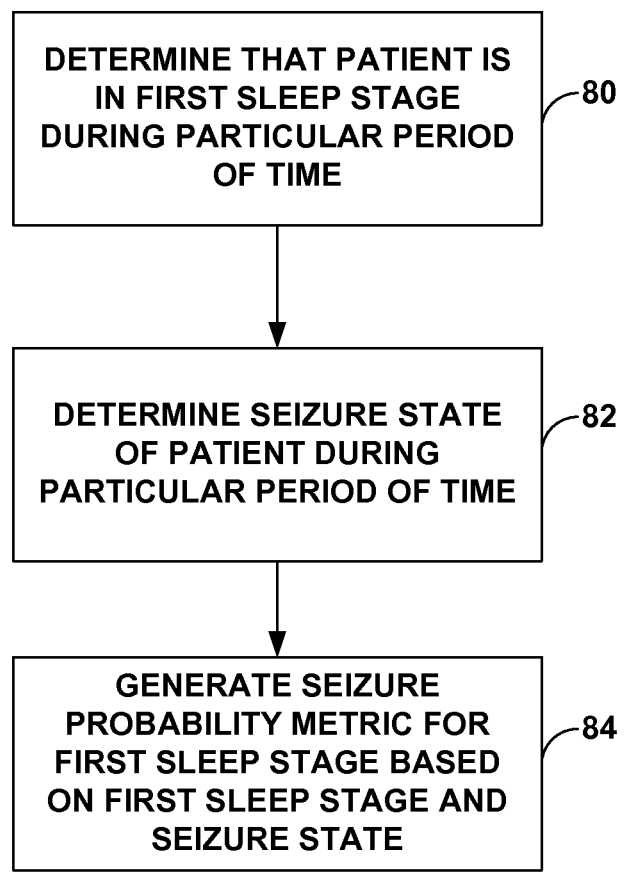
FIG. 5 is a flow diagram illustrating an example technique for generating an example seizure probability metric for a particular sleep stage of a patient.

FIG. 5 is a flow diagram illustrating an example technique for generating a seizure probability metric for a particular sleep stage of patient 12. While FIG. 5 is described as being performed by a component of processor 42, in other examples, a processor of another device described herein, e.g., processor 70 of programmer 14, may additionally or alternatively perform any part of the technique shown in FIG. 5 alone or with the aid of a user.

In accordance with the technique illustrated in FIG. 5, sleep stage detection module 54 may determine that patient 12 is in a first sleep stage during a first period of time (80). For example, as described previously, sleep stage detection module 54 may determine whether patient 12 is in an awake stage, a N1 sleep stage, a N2 sleep stage, a Deep Sleep stage (e.g., a N3 sleep stage or N4 sleep stage), or a REM sleep stage. Sleep stage detection module 54 may determine the sleep stage of patient 12 using any suitable technique, including those described in this disclosure. For example, as discussed previously, sleep stage detection module 54 may determine a sleep stage of patient 12 by analyzing a frequency characteristic of a bioelectrical brain signal (e.g., a power level or energy within one or more frequency bands of the bioelectrical brain signal, a ratio of the power level in two or more frequency bands, a correlation in change of power between two or more frequency bands, a pattern in the power level of one or more frequency bands over time, and the like) of patient 12. Sleep stage detection module 54 may determine when patient 12 enters a different sleep stage other than the first sleep stage to determine the duration of the first time period that patient 12 was in the first sleep stage.

In addition to sleep stage detection module 54 determining that patient 12 is in a first sleep stage during the particular period of time (80), seizure state detection module 55 may determine the seizure state of patient 12 during the particular period of time (82). For example, seizure state detection module 55 may determine whether or not patient 12 experienced a seizure during the particular period of time patient 12 when occupied the first sleep stage. In some examples, if seizure state detection module 55 determines that patient 12 experienced a seizure during the particular period of time, seizure state detection module 55 may determine that patient 12 was in a first seizure state during the particular period of time. If seizure state detection module 55 determines that patient 12 did not experience a seizure during the particular period of time, seizure state detection module 55 may determine that patient 12 was in a second seizure state during the particular period of time.

Seizure state detection module 55 may determine a seizure state of patient 12 using any suitable technique, including those techniques describe above in this disclosure. For example, as discussed previously, seizure state detection module 55 may implement a seizure detection algorithm to determine whether a bioelectrical brain signal of patient 12 sensed when patient 12 was in the first sleep stage exhibits one or more characteristics previously determined to be indicative of a seizure event. In other examples, as also described above, seizure state detection module 55 may detect a seizure based on other parameters, such as impedance of brain 24, the physical movement of patient 12, and/or intracranial pressure of patient 12.

In some examples, seizure state detection module 55 and sleep stage detection module 54 may determine the seizure state and sleep stage, respectively, of patient 12 based on the same sensed parameter of patient 12. For example, seizure state detection module 55 and sleep stage detection module 54 may determine the seizure state and sleep stage, respectively, of patient 12 based on one or more sensed bioelectrical brain signals of patient 12. In other examples, seizure state detection module 55 and sleep stage detection module 54 may determine the seizure state and sleep stage, respectively, of patient 12 based on different sensed parameters of patient 12. For example, seizure state detection module 55 may determine the seizure state of patient 12 based on the signal output of one or more patient motion sensor (e.g., an accelerometer sensor) and sleep stage detection module 54 may determine the sleep stage of patient 12 based on a sensed bioelectrical brain signals of patient 12.

According to the example technique illustrated in FIG. 5, upon determining the seizure state of patient 12 during the particular period of time, seizure probability metric generation module 56 may generate a seizure probability metric for the first sleep stage based at least in part on the seizure state of patient 12 during the particular sleep stage (84). The seizure probability metric for the first sleep stage may indicate the probability or susceptibility of patient 12 to a seizure event during the first sleep stage. In some examples, the seizure probability metric may be used to modify one or more therapy parameters, such as monitoring parameters or therapy parameters, to more effectively treat the seizure disorder of patient 12 based on a sleep stage of patient 12. Seizure probability metric generation module 56 generates a seizure probability metric for the first sleep stage using any suitable technique to reflect the probability of patient 12 experiencing a seizure when in the first sleep stage. For example, in some examples, as discussed in further detail with respect to FIG. 6, seizure probability metric generation module 56 may access data stored in a seizure log, e.g., seizure log 57, for the first sleep stage and may determine the seizure probability metric for the first sleep stage based on the stored data.

While the example of FIG. 5 is described with regard to generating a seizure probability metric for only a first stage, as will be described below, such a technique may be employed by system 10 to generate a seizure probability metric for each of a plurality of sleep stages of patient 12. The plurality of sleep stages that seizure probability may include substantially all or at least some of the sleep stages that may be experienced by patient 12. In cases in which a seizure probability metric is generated for each of a plurality of sleep stage experienced by patient 12, the seizure probability metric may be used to reflect the probability of patient 12 experiencing a seizure during a particular sleep stage relative to one more other sleep stages.

Moreover, while the example technique of FIG. 5 is described with regard to generating a seizure probability metric based on the seizure state detected for a single occurrence of patient being in the first sleep stage, in some example, seizure probability metric generation module 56 may generate a seizure probability metric based on the seizure state of patient determined for each of a plurality of times patient 12 occupies the first sleep stage. In some examples, the seizure probability metric for the first sleep stage may be a dynamic value that is updated periodically or continuously by seizure probability metric generation module 56 as time passes and the number of occurrences of patient 12 being in the first sleep stage increases.

Figure 6:
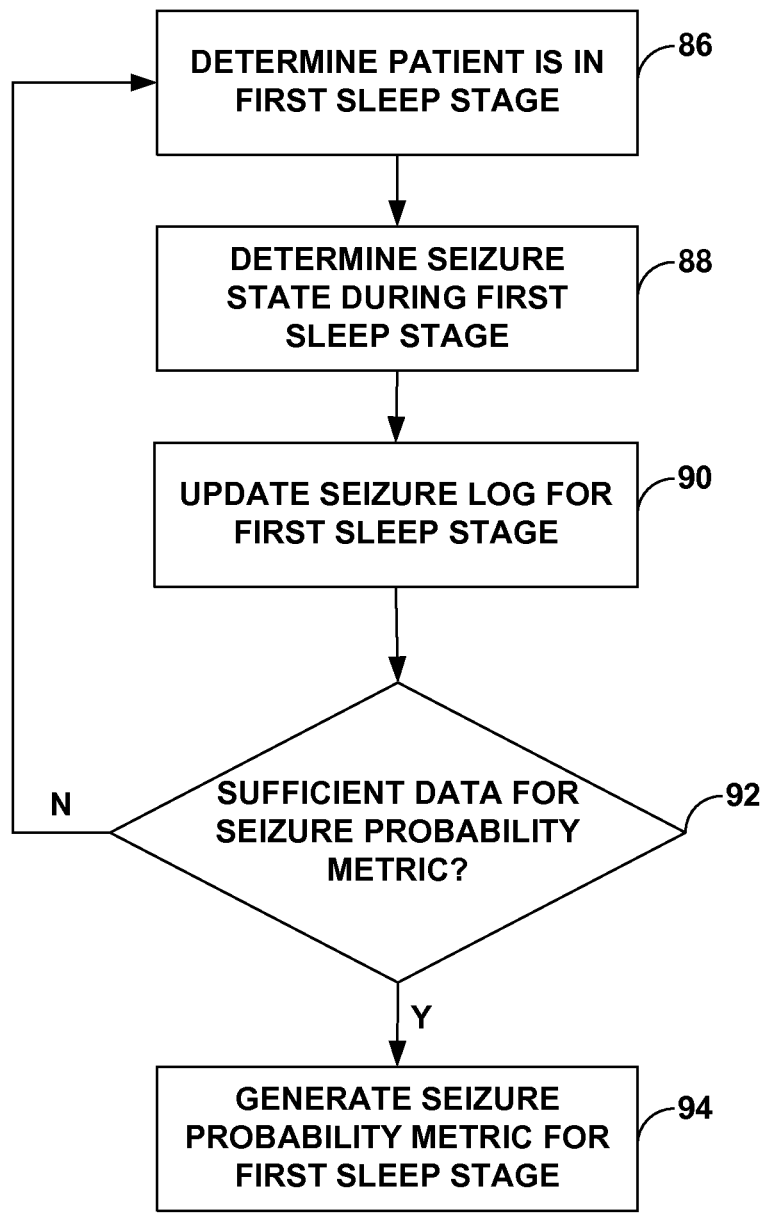
FIG. 6 is a flow diagram illustrating an example technique for generating an example seizure probability metric for a particular sleep stage of a patient using an example seizure log.

FIG. 6 is a flow diagram illustrating an example technique for generating the seizure probability metric for the first sleep stage based on storing data in a seizure log. While FIG. 6 is described as being performed by a component of processor 42, in other examples, a processor of another device described herein, e.g., processor 70 of programmer 14, may additionally or alternatively perform any part of the technique shown in FIG. 6 alone or with the aid of a user.

In the example technique illustrated in FIG. 6, sleep stage detection module 54 may determine that patient 12 is in a first sleep stage (86), using any suitable technique. Additionally, seizure state detection module 55 determines the seizure state of patient 12 during the first sleep stage (88), using any suitable technique.

As discussed previously with respect to FIGS. 2 and 3, in some examples, IMD 16 includes a seizure log 57, which stores data correlating one or more seizure states of patient 12 to one or more sleep stages of patient 12. For example, seizure log 57 may include a seizure log for a particular sleep stage, and seizure state detection module 55 may update the seizure log based on the seizure state of patient 12 determined while patient 12 was in the particular sleep stage for each of a plurality of different instances in which patient experienced the particular sleep stage. Collecting such data for multiple different instances during which patient 12 experienced a particular sleep stage may provide a more accurate seizure probability metric for the particular sleep stage, e.g., by providing a more accurate indication of the likelihood that patient 12 will experience a seizure event during a particular sleep stage, in comparison to collecting data during only one or very few periods of time.

Upon determining the seizure state of patient 12 during the first sleep stage, seizure state detection module 55 may update seizure log 57 for the first sleep stage (90). As an example, seizure log 57 may include a first counter indicative of the number of time periods in which patient 12 has experienced the first sleep stage and a second counter indicative of the number of times patient 12 has experienced a seizure while experiencing the first sleep stage. If seizure state detection module 55 determines that patient 12 experienced a seizure during a particular instance of experiencing the first sleep stage, seizure state detection module 55 may increment the first counter indicative of patient 12 experiencing the first sleep stage and the second counter indicative of patient 12 experiencing a seizure event while experiencing the first sleep stage. On the other hand, if seizure state detection module 55 determines that patient 12 did not experience a seizure during the particular instance of the first sleep stage, seizure state detection module 55 may increment only the first counter indicative of patient 12 experiencing the first sleep stage, and may not increment the second counter indicative of patient 12 experiencing a seizure. In other examples, seizure state detection module 55 may update the seizure log for the first sleep stage in another manner such that data correlating the first sleep stage to seizure states of patient 12 during the first sleep stage are stored.

Upon updating seizure log 57 for the first sleep stage, processor 42 determines whether sufficient data have been collected for generating a seizure probability metric for the first sleep stage (92). For example, processor 42 may determine whether seizure state detection module 55 has determined the seizure state of patient 12 during the first sleep stage during at least a predetermined number of different time periods in which patient 12 experienced the first sleep stage and/or whether seizure state detection module 55 has updated seizure log 57 for the first sleep stage at least a predetermined number of times. Such a threshold number for generating a seizure probability metric may be defined via any suitable technique. For example, such a threshold number programmed by a clinician or other user during a programming session. In some examples, the threshold number may be defined to generally correspond to the number of occurrences of patient 12 experiencing the first sleep stage for the generated seizure probability metric to be a statistically significant probability value. The same threshold number for generating a seizure probability profile may be used for all patient sleep stages, or a threshold number may be unique to one or more sleep stage of patient 12.

If processor 42 determines that sufficient data has not been collected, processor 42 may continue to collect more data by repeating such a process for one more future periods in which patient 12 experiences a first sleep stage until sufficient data for generating a seizure probability metric has been collected (92).

If, on the other hand, processor 42 determines that sufficient data have been collected, seizure probability metric generation module 56 may generate a seizure probability metric for the first sleep stage based on the data stored in seizure log 57 (94). The seizure probability metric may be any metric indicative of the likelihood that patient 12 will experience a seizure event during the first sleep stage or the susceptibility of patient 12 to a seizure event during the first sleep stage.

In some examples, processor 42 may utilize a seizure probability metric for one or more sleep stages to tailor the therapy provided to patient 12 via IMD 16, e.g., by adjusting one or more aspects related to the monitoring for patient seizure events and/or related to the delivery of stimulation therapy. While the example of FIG. 6 illustrates a seizure probability metric being generated by seizure probability metric generation module 56 (94) only after a sufficient amount of data has been collected (92), in other examples, seizure probability metric generation module 56 may generate a seizure probability metric regardless of whether a sufficient amount of data has been collected. However, in such examples, seizure probability metric generation module 56 may dynamically update the seizure probability metric as additional data is collected, and processor 44 may only adjust one or more aspects of the therapy provided to patient 12 by system 10 (e.g., in terms of seizure monitoring and/or stimulation therapy parameters) only after a sufficient amount of data has been collected.

In some examples, seizure probability metric generation module 57 may analyze the data stored in seizure log 57 to generate a numerical value indicative of the probability that patient 12 will experience a seizure event during a time period in which patient 12 experiences the first sleep stage. For example, in examples in which seizure log 57 includes a first counter indicative of the number of time periods in which patient 12 has experienced the first sleep stage and a second counter indicative of the number of times patient 12 has experienced a seizure while experiencing the first sleep stage, seizure probability metric generation module 56 may calculate the percentage of time periods in which patient 12 experienced the first sleep stage that patient 12 also experienced a seizure event. As an example, if the first counter within seizure log 57 indicates that patient 12 experienced the first sleep stage during ten different time periods and the second counter within seizure log 57 indicates that patient 12 experienced a seizure event during four (of the ten) time periods, seizure probability metric generation module 56 may generate a seizure probability metric indicating that patient 12 has an approximately 40% chance of experiencing a seizure event during time periods in which patient 12 experiences the first sleep stage.

Although the technique illustrated in FIG. 6 includes steps for generating a seizure probability metric for only one sleep stage of patient 12, in other examples, seizure probability metric generation module 56 may generate seizure probability metrics for a plurality of sleep stages of patient 12, e.g., by repeating the technique illustrated in FIG. 6 for each of the plurality of sleep stages. For example, processor 42 may create a seizure probability profile, e.g., seizure probability profile 58, for patient 12 that includes a plurality of seizure probability metrics corresponding to each of the plurality of sleep stages for patient 12. In some examples, the seizure probability profile may be used as a reference to modify treatment parameters of patient 12. The seizure probability profile may also be useful in comparing susceptibility of patient 12 to seizures during different sleep stages, e.g., to determine whether patient 12 may be most susceptible to a seizure event.

Figure 7:
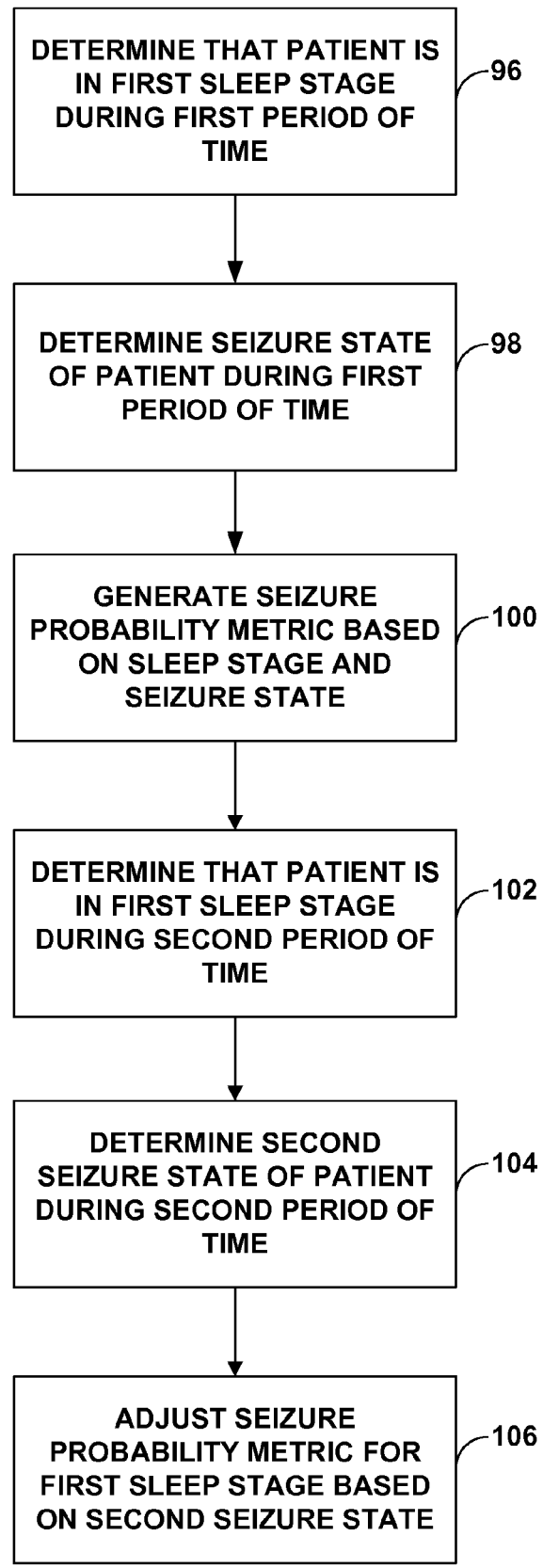
FIG. 7 is a flow diagram illustrating an example technique for adjusting an example seizure probability metric for a particular sleep stage based on detecting multiple seizure states correlating to the particular sleep stage.

While the example of FIG. 6 illustrates the seizure probability metric for the first sleep stage as being a generally static value after being generated, in other examples, the seizure probability metric for the first sleep stage may be a dynamic value (or a value that can change over time). For example, seizure probability metric generation module 56 may update the seizure probability metric on a substantially continuous or periodic basis as additional data for the first sleep stage is collected FIG. 7 illustrates an example technique that may be performed by processor 42 to adjust a seizure probability metric generated for a first sleep stage, based on collecting additional seizure state data. While FIG. 7 is described as being performed by a component of processor 42, in other examples, a processor of another device described herein, e.g., processor 70 of programmer 14, may additionally or alternatively perform any part of the technique shown in FIG. 7 alone or with the aid of a user.

According to the technique illustrated in FIG. 7, sleep stage detection module 54 may determine that patient 12 is in a first sleep stage during a first period of time (96), using any suitable sleep stage detection technique. Seizure state detection module 55 may also determine the seizure state of patient 12 while patient is in the first sleep stage during the first period of time (98), using any suitable technique. Upon determining the seizure state of patient 12 during the first period of time, seizure probability metric generation module 56 generates a seizure probability metric for the first sleep stage (100). In some examples, seizure probability metric generation module 56 may generate a seizure probability metric for the first sleep stage using a technique similar to the technique illustrated in FIG. 6, which may include determining the seizure state of patient 12 for each of multiple different instances in which patient 12 is in the first sleep stage and updating a seizure log until sufficient data is collected to generate a seizure probability metric.

Although seizure probability metric generation module 56 has already generated a seizure probability metric for the first sleep stage (100), in some examples, seizure state detection module 55 may continue to monitor the seizure state of patient 12 during additional time periods in which patient 12 experiences the first sleep stage. In such a case, sleep stage detection module 54 may subsequently determine that patient 12 is in the first sleep stage during a second period of time (102), and seizure state detection module 55 may also determine the seizure state of patient 12 while patient 12 is in the first sleep stage during the second period of time (104). In some examples, the additional seizure state data may indicate that the susceptibility or probability of patient 12 to experience a seizure event is different than indicated by the previously generated seizure probability metric. Consequently, in order that the seizure probability metric most accurately portrays the probability that patient 12 will experience a seizure during the first sleep stage, processor 42 may adjust the seizure probability metric based on the second determined seizure state for the first sleep stage (106).

As an example, seizure probability metric generation module 56 may generate a seizure probability metric indicating that patient 12 has a 40% chance of experiencing a seizure event during the first sleep stage. Sleep stage detection module 54 may continue to determine the sleep stage of patient 12 and seizure state detection module 55 may continue to determine the seizure state of patient 12 during the determined sleep stages. If seizure state detection module 55 determines that a seizure state of patient 12 correlated to the first sleep stage would change the percentage chance that patient 12 would experience a seizure event during the first sleep stage to a percentage greater than or less than 40%, processor 42 may adjust the percentage value (i.e., the seizure probability metric, in this example) for the first sleep stage. In this manner, for example, seizure probability metric generation module 56 may dynamically update the seizure probability metric for one or more sleep stages over a period of time. In some examples, a seizure probability metric may the dynamically updated to reflect all of the sleep stage and seizure state data collected and/or may be dynamically updated to reflect only a portion of the sleep stage and seizure state data collected (e.g., using a rolling window of time using the most recent data, such as, the last week, month, or year of collected data, while not including relatively old data).

Figure 8:
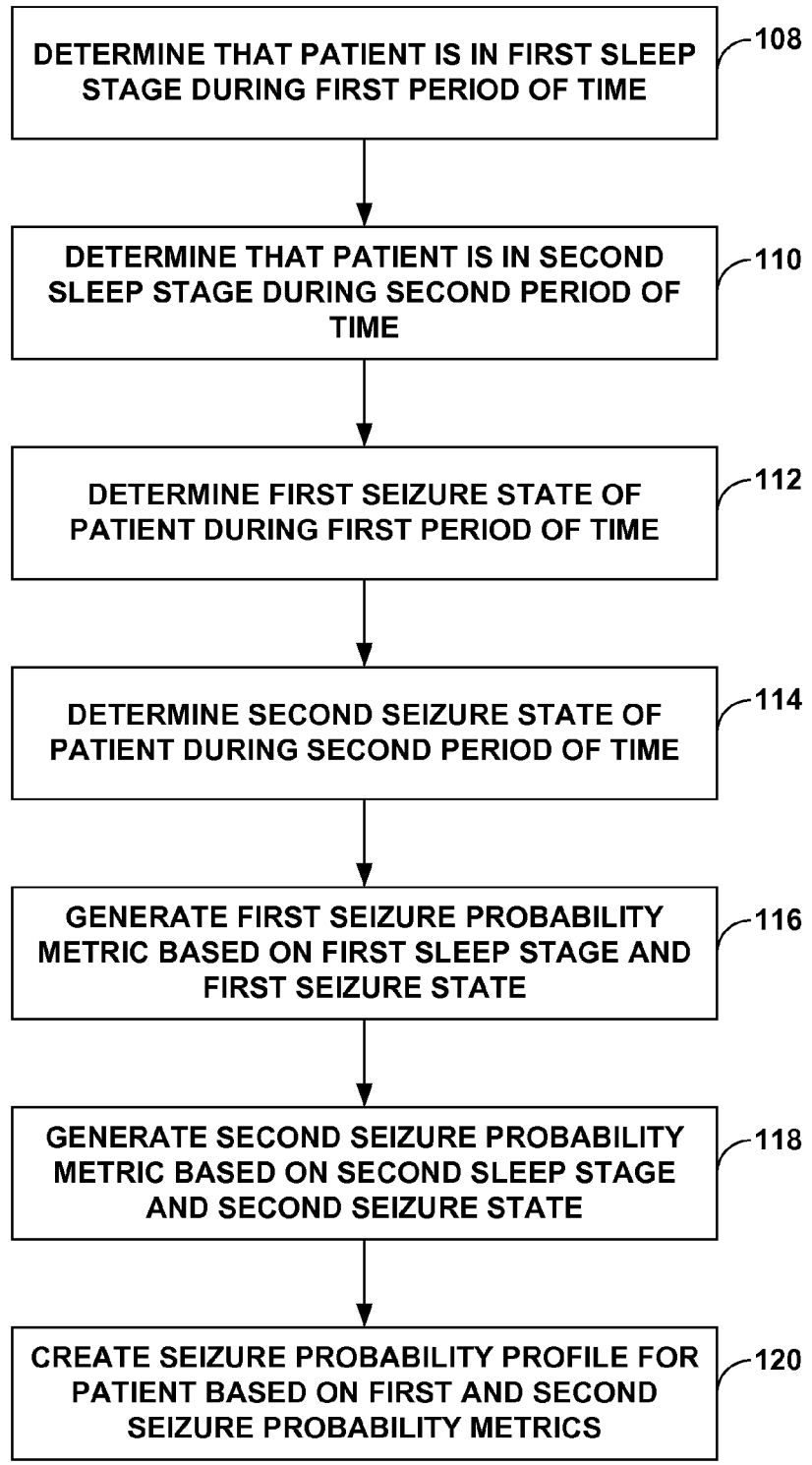
FIG. 8 is a flow diagram illustrating an example technique for creating an example seizure probability profile for a patient.

FIG. 8 illustrates an example technique that may be performed by processor 42 to create a seizure probability profile for patient 12 based on seizure probability metrics for multiple sleep stages. While FIG. 8 is described as being performed by a component of processor 42, in other examples, a processor of another device described herein, e.g., processor 70 of programmer 14, may additionally or alternatively perform any part of the technique shown in FIG. 8 alone or with the aid of a user.

According to the technique illustrated in FIG. 8, sleep stage detection module 54 determines that patient 12 is in a first sleep stage during a first period of time (108) and a second sleep stage during a second period of time (110) using any suitable technique(s). Seizure state detection module 55 subsequently determines a first seizure state of patient 12 during the first period of time (112) and a second seizure state of patient 12 during the second period of time (114) using any suitable technique(s). Seizure probability metric generation module 56 generates a first seizure probability metric based on at least the first seizure state of patient 12 during the first sleep stage (116) and a second seizure probability metric based on at least the second seizure state of patient 12 during the second sleep stage (118) using any suitable technique(s). As discussed previously, the seizure probability metrics can indicate the likelihood or probability that patient 12 may experience a seizure event during a particular sleep stage, or the susceptibility of patient 12 to a seizure event during the particular sleep stage. As described, such a seizure probability metric for a particular sleep stage may be generated based on the past seizure history of patient 12 when experiencing the particular sleep stage.

Upon generating the first and second seizure probability metrics, processor 42 may create a seizure probability profile for patient 12 based on the first and second seizure probability metrics (120). In some examples, the seizure probability profile for patient 12 defines a plurality of seizure probability metrics, each of which may be correlated to a respective sleep stage. By defining a seizure probability profile based on sleep probability metrics generated for multiple sleep stages, the profile may generally reflect the absolute probability of patient 12 experiencing a seizure during respective sleep stages and/or may generally reflect the probability of patient 12 experiencing a seizure during a respective sleep stage relative to one more other sleep stages of the profile.

The seizure probability profile can be used as a resource, e.g., by processor 42 and/or a clinician, to generate modifications to treatment parameters based on a sleep stage of patient 12. In this way, the treatment parameters may be specialized to the seizure disorder of patient 12, which may create a more patient-specific treatment regimen and, consequently, a more effective treatment regimen. For example, as discussed in further detail with respect to FIG. 9, processor 42 may modify a seizure detection algorithm based on one or more seizure probability metrics, e.g., stored in a seizure probability profile for patient 12. As another example, as discussed in further detail with respect to FIG. 10, processor 42 may adjust one or more parameters of therapy based on one or more seizure probability metrics, e.g., stored in a seizure probability profile for patient 12. In either case, such modifications may be made based on manually inputted direction of a clinician and/or automatically or semi-automatically modified by processor 42 of IMD 42, e.g., in view of the seizure probability metric for a sleep stage during the time period sleep stage detection module 54 determines patient 12 is in the respective sleep stage.

In some examples, a seizure probability profile may be defined by the respective seizure probability metrics generated for substantially all sleep stage of patient 12. In some examples, a seizure probability metric may be defined for each of the awake stage, Stage 1 sleep stage, Stage 2 sleep stage, a Deep Sleep stage (or separately as Stage 3 and Stage 4)), and REM sleep stage. In such an example, the seizure probability profile for patient 12 may be defined by the seizure probability metric for each respective sleep stage of patient 12. Similar to that described above, the seizure probability profile may be dynamically updated by dynamically updating one or more of the seizure probability metric used to define the profile as additional data is collected over time.

In some examples, the seizure probability profile may be presented to a user, e.g., a clinician, via a display, e.g., user interface 76 of programmer 14. Based on viewing the seizure probability profile, the user may provide input regarding the treatment of patient 12, e.g., may modify one or more treatment parameters based on the seizure probability profile. For example, the user may generate a respective therapy program for each of the sleep stages of patient 12 based on information in the seizure probability profile for patient 12 that indicates the likelihood that patient 12 will experience a seizure during each of the sleep stages. In another example, when the seizure probability profile indicates substantially the same probability of patient experiencing a seizure for substantially all sleep stages, a clinician may program IMD 16 to deliver substantially the same therapy and monitor for seizures using substantially the same detection algorithm for each sleep stage of patient 12.

Figure 9:
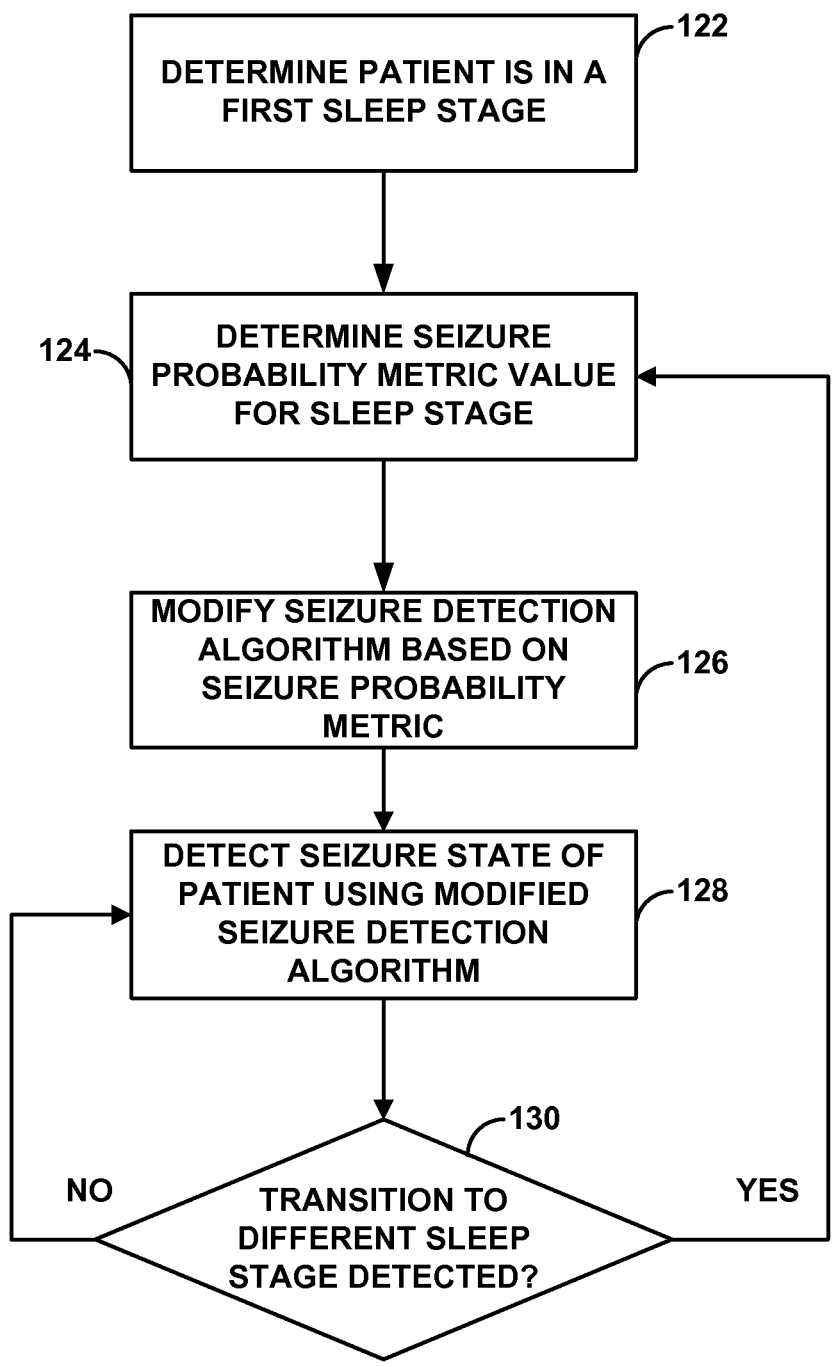
FIG. 9 is a flow diagram illustrating an example technique for modifying an example seizure detection algorithm based on a seizure probability metric.

FIG. 9 illustrates an example technique that may be performed by processor 42 to modify a seizure detection algorithm based on a seizure probability metric. While FIG. 9 is described as being performed by a component of processor 42, in other examples, a processor of another device described herein, e.g., processor 70 of programmer 14, may additionally or alternatively perform any part of the technique shown in FIG. 9 alone or with the aid of a user.

Figure 10:
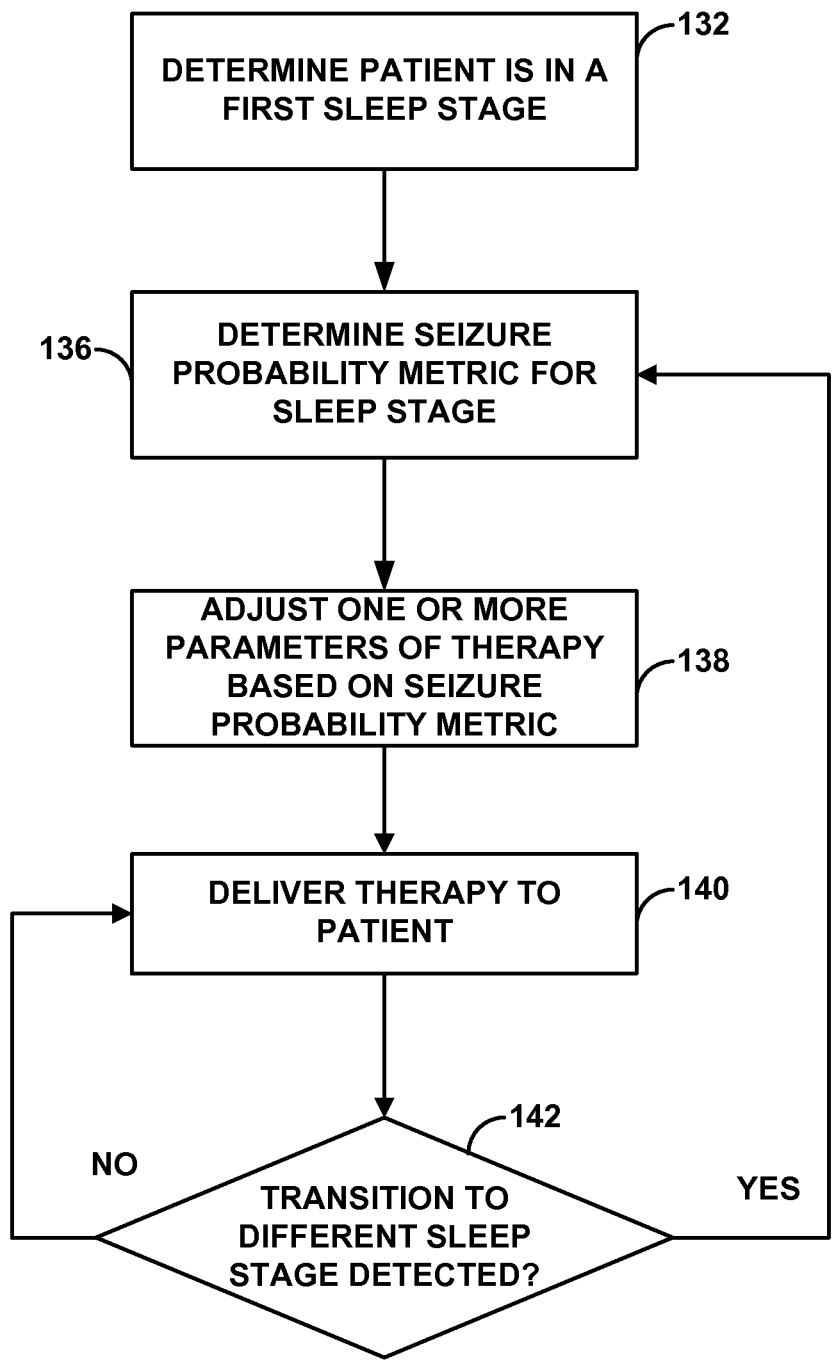
FIG. 10 is a flow diagram illustrating an example technique for adjusting one or more example therapy parameters based on an example seizure probability metric.

For ease of illustration the examples of FIGS. 9 and 10 are described for cases in which a seizure probability metric has been generated for each sleep stage of patient 12. As such, in some instances, prior to employing such techniques, a seizure probability metric may be first generated for each sleep stage of patient, e.g., using one or more of the techniques described herein. In other examples, relatively conservative baseline seizure probability metrics may be defined for one or more sleep stages rather than generating the seizure probability metrics for the sleep stages based on the history of patient 12. For example, such an approach may be used initially upon implanting IMD 16 within patient 12 when such sleep stage/seizure state data may not be available. In such examples, the seizure probability metric for one or more of the sleep stages of patient 12 may be updated over time as sufficient sleep stage/seizure state data is collected.

In the example technique illustrated in FIG. 9, initially, sleep stage detection module 54 may determine that patient 12 is in a first sleep stage during a first period of time (122). Prior to this determination, seizure state detection module 55 may use a baseline or default seizure detection algorithm to determine the seizure state of patient 12, e.g., one that is not specific to any seizure probability metric. Based on the determination that patient 12 is in the first sleep stage, processor 42 may determine the value of the seizure probability metric defined for the first sleep stage (124). Such a value may have been generated previously by seizure probability metric generation module (e.g., as described above), and may be stored in memory 40.

Based on the seizure probability metric for the first sleep stage, processor 42 modifies the seizure detection algorithm used by seizure state detection module 55 to determine the seizure state of patient 12 (126). As described above, the value of the seizure probability metric may be indicative of the probability or susceptibility of patient 12 experiencing a seizure while in the first sleep stage. As such, processor 40 may modify the seizure detection algorithm from that being currently employed to detect the seizure state of patient 12 consistent with the probability of patient 12 experiencing a seizure while in the first sleep stage, as reflected by the seizure probability metric for the first sleep stage.

For example, processor 40 may adjust the seizure detection algorithm to be more sensitive, e.g., when sleep stage detection module 55 determines that patient 12 is in a sleep stage with a seizure probability metric that indicates a relatively high probability of patient 12 experiencing a seizure. In other examples, processor 40 may adjust a seizure detection algorithm to be less sensitive, e.g., when sleep stage detection module 55 determines that patient 12 is in a sleep stage with a seizure probability metric that indicates a relatively low probability of patient 12 experiencing a seizure.

Seizure state detection module 55 may then use the modified seizure detection algorithm to monitor and detect seizures in brain 28 of patient 12 (128), e.g., based on an analysis of bioelectrical brain signals of patient 12 using the modified seizure detection algorithm. Seizure state detection module 55 may used the modified detection algorithm until sleep state detection module determines that patient 12 has transitioned to another steep stage (130). When seizure state detection module 55 determines that patient 12 is in a new sleep stage, then processor 42 may determine the seizure probability metric value for the new sleep stage (124), and modify the seizure detection algorithm used by seizure state detection module 55 to determine the seizure state of patient 12 based on the seizure probability metric value for the new sleep stage (126), as described above.

In some examples, processor 42 may activate and/or suspend the operation of seizure state detection module 55 based on a seizure probability metric. When active, processor 42 may use seizure state detection module to monitor the seizure state of patient 12, e.g., to detect when patient 12 experiences a seizure. Conversely, when suspended, processor 42 may not be actively monitoring the seizure state of patient 12. In some examples, processor 42 may be configured to suspend the detection of the seizure state of patient 12 when a patient occupies a sleep stage with a relatively low seizure probably metric, e.g., when the seizure probability metric indicates that patient 12 has not experienced a seizure while in the seizure state. Similarly, processor 42 may be configured to activate the detection of the seizure state of patient 12 when a patient occupies a sleep stage with a relatively high seizure probably metric, e.g., when the seizure probability metric indicates that patient 12 has experienced a high frequency of seizure while in the particular seizure state. In this manner, IMD 16 may more efficiently detect the occurrence of seizures in patient 12.

FIG. 10 illustrates an example technique that may be performed by processor 42 to adjust one or more therapy parameters based on a seizure probability metric. While FIG. 10 is described as being performed by a component of processor 42, in other examples, a processor of another device described herein, e.g., processor 70 of programmer 14, may additionally or alternatively perform any part of the technique shown in FIG. 10 alone or with the aid of a user.

In the example technique illustrated in FIG. 10, initially, sleep stage detection module 54 may determine that patient 12 is in a first sleep stage during a first period of time (132). Prior to this determination, processor 42 may control stimulation generator 44 to deliver stimulation therapy to patient 12 according to one more baseline or default therapy programs (e.g., one that is not specific to any seizure probability metric) to treat a seizure disorder of patient 12. Based on the determination that patient 12 is in the first sleep stage, processor 42 may determine the value of the seizure probability metric defined for the first sleep stage (136). Such a value may have been generated previously by seizure probability metric generation module (e.g., as described above), and may be stored in memory 40.

Based on the seizure probability metric for the first sleep stage, processor 42 may modify one or more parameters of the stimulation therapy being delivered to brain 28 of patient 12 via IMD 16 (138). As described above, the value of the seizure probability metric may be indicative of the probability or susceptibility of patient 12 experiencing a seizure while in the first sleep stage. As such, processor 40 may modify the stimulation being delivered to brain 28 to treat or otherwise manage a seizure disorder of patient 12 consistent with the probability of patient 12 experiencing a seizure while in the first sleep stage, as reflected by the seizure probability metric for the first sleep stage.

For example, if the seizure probability metric indicates that patient 12 is more susceptible to experiencing a seizure event during the first sleep stage, processor 42 may adjust the therapy increase the aggressiveness of therapy delivered to patient 12 during time periods in which sleep stage detection module 54 determines that patient 12 is in the first sleep stage. In examples in which IMD 16 delivers electrical stimulation to brain 24 of patient 12 via electrodes 22A, 22B, processor 42 may increase one or more parameters defining the electrical stimulation, e.g., amplitude or frequency, in order to increase the aggressiveness of the electrical stimulation treatment. In examples in which IMD 16 delivers drug therapy to treat the seizure disorder of patient 12, processor 42 may increase a drug dosage delivered to patient 12 in order to increase the aggressiveness of the therapy.

Similarly, in examples in which the seizure probability metric indicates that patient 12 is less susceptible to experiencing a seizure event during the first sleep stage, processor 42 may adjust the therapy to decrease the aggressiveness of therapy delivered to patient 12 during time periods in which sleep stage detection module 54 determines that patient 12 is in the first sleep stage, e.g., by decreasing one or more parameters of electrical stimulation or decreasing a dosage of a drug delivered to patient 12 to treat the seizure disorder. In other examples, processor 42 may adjust another parameter of therapy delivery based on the seizure probability metric for the first sleep stage. For example, processor 42 may control delivery of therapy to a different location within the body of patient 12, e.g., via a different combination of electrodes 22A, 22B, based on determining that patient 12 is in the first sleep stage.

In some examples, processor 40 may modify the stimulation therapy being delivered to patient 12 by adjusting one or more parameters defined by a therapy program (e.g., frequency, amplitude (current or voltage), duration, duty cycle, electrode polarity, and the like) being used to control the stimulation being delivered to patient 12, and/or change to a different therapy program to control stimulation while patient 12 is in the first sleep stage. Additionally or alternatively, patient 12 may change the location of brain 28 where the stimulation is being delivered to patient 12 by IMD 14, e.g., by changing the electrode combination being used to deliver stimulation to brain 28.

Processor 44 may then control the delivery of stimulation to brain 28 of patient 12 according to the adjustments made to the therapy (140). Processor 42 may control the delivery of stimulation to patient 12 according to the adjusted therapy (140) until sleep state detection module determines that patient 12 has transitioned to another sleep stage (1342). When seizure state detection module 55 determines that patient 12 is in a new sleep stage, processor 42 may determine the seizure probability metric value for the new sleep stage (136), and modify the therapy delivered to patient 12 based on the seizure probability metric value for the new sleep stage (138), as described above.

Processor 44 may modify the therapy delivered to patient 12 by suspending the delivery of therapy, initiating the delivery of therapy, or adjusting one or more parameters of therapy delivered to patient 12 based on the seizure probability metric corresponding to the sleep stage occupied by patient 12. For examples in which the therapy is delivered in the form of electrical stimulation, processor 44 may modify one or more of the duty cycle, amplitude, frequency, electrode configuration, duration (e.g., pulse width), and/or other stimulation parameter based on the seizure probability metric corresponding to the sleep stage occupied by patient 12. In cases in which the seizure probability metric for the sleep stage occupied by patient 12 reflects a relatively low probability (e.g., substantially zero) of patient 12 experiencing a seizure, processor 44 may suspend the delivery of electrical stimulation to brain 24 of patient 16 delivered to treat the patient disorder while patient occupies the particular sleep stage. Conversely, in cases in which the seizure probability metric for the sleep stage occupied by patient 12 reflects a relatively high probability of patient 12 experiencing a seizure, processor 44 may initiate the delivery of electrical stimulation to brain 24 of patient 16 delivered to treat the patient disorder while patient occupies the particular sleep stage.

In examples in which IMD 16 is already delivering electrical stimulation to patient 12, for example, processor 44 may modify one or more parameters of the electrical stimulation to brain 24 of patient 16 delivered to treat the patient disorder while patient occupies the particular sleep stage. For example, processor 42 may shorten the duty cycle of the stimulation, increase the amplitude of the stimulation, and/or increase pulse width of the stimulation when patient 12 enters a sleep stage with a seizure probability metric that indicates a relatively high probability of patient 12 experiencing a seizure. Similarly, processor 42 may increase the duty cycle of the stimulation, decrease the amplitude of the stimulation, and/or decrease pulse width of the stimulation when patient 12 enters a sleep stage with a seizure probability metric that indicates a relatively low probability of patient 12 experiencing a seizure.

For cases in which IMD 16 delivers therapy in the form of drug delivery, processor 42 may withhold or reduce the infusion rate and/or concentration of the drug delivered when patient 12 enters a sleep stage with a seizure probability metric that indicates a relatively low probability of patient 12 experiencing a seizure. Similarly, processor 42 may initiate or increase the infusion rate and/or concentration of the drug delivered when patient 12 enters a sleep stage with a seizure probability metric that indicates a relatively high probability of patient 12 experiencing a seizure. Additionally or alternatively, processor 42 may deliver one or more boluses when patient 12 enters a sleep stage with a seizure probability metric that indicates a relatively high probability of patient 12 experiencing a seizure.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to support one or more aspects of the functionality described in this disclosure.

If implemented in software, the techniques described in this disclosure may be stored on or transmitted over as one or more instructions or code on a computer-readable medium. Computer-readable media may include non-transitory computer storage media or communication media including any medium that facilitates transfer of a computer program from one place to another. Data storage media may be any available media that can be accessed by one or more computers or one or more processors to retrieve instructions, code and/or data structures for implementation of the techniques described in this disclosure. By way of example, and not limitation, such data storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The code may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

In addition, it should be noted that the systems described herein may not be limited to treatment of a human patient. In alternative examples, these systems may be implemented in non-human patients, e.g., primates, canines, equines, pigs, and felines. These animals may undergo clinical or research therapies that my benefit from the subject matter of this disclosure.

Various examples have been described. These and other examples are within the scope of the following claims.

What is claimed is:
1. A method comprising:

determining, with one or more medical devices, that a patient is in a first sleep stage during a first period of time;

determining, with the one or more medical devices, a first seizure state of the patient, wherein the first seizure state of the patient comprises a seizure state of the patient during the first period of time; and generating, with the one or more medical devices, a first seizure probability metric for the first sleep stage based on at least the first sleep stage and the first seizure state.

2. The method of claim 1, wherein determining a first seizure state of the patient comprises determining the first seizure state of the patient based on a bioelectrical brain signal of the patient sensed by the one or more medical devices.

3. The method of claim 1, further comprising:
determining that the patient is in a second sleep stage during a second period of time;
determining a second seizure state of the patient, wherein the second seizure state of the patient comprises a seizure state of the patient during the second period of time;
generating a second seizure probability metric for the second sleep stage based on at least the second sleep stage and the second seizure state; and
creating a seizure probability profile for the patient based on at least the first and second seizure probability metrics.

4. The method of claim 3, wherein the seizure probability profile for the patient comprises the first and second seizure probability metrics.

5. The method of claim 1, wherein determining the first seizure state of the patient comprises evaluating a bioelectrical brain signal of the patient via a seizure detection algorithm to determine whether the patient experienced a seizure during the first period of time.

6. The method of claim 5, further comprising adjusting the seizure detection algorithm based on at least the first seizure probability metric.

7. The method of claim 1, further comprising:
delivering therapy to the patient to treat a seizure disorder of the patient; and
adjusting at least one parameter of the therapy based on the first seizure probability metric.

8. The method of claim 7, wherein adjusting at least one parameter of the therapy based on the first seizure probability metric comprises suspending the delivery of therapy when the patient occupies the first sleep stage.

9. The method of claim 1, wherein the sleep stage comprises an N1 sleep stage, an N2 sleep stage, a Deep Sleep stage, a rapid eye movement (REM) sleep stage, or an awake stage.

10. The method of claim 1, wherein generating the first seizure probability metric comprises generating a metric indicative of susceptibility of the patient to seizure events during the first sleep stage.

11. The method of claim 1, further comprising:
determining that the patient is in the first sleep stage during a second period of time;
determining a second seizure state of the patient, wherein the second seizure state of the patient comprises a seizure state of the patient during the second period of time; and
adjusting the first seizure probability metric for the first sleep stage based on at least the second seizure state.

12. A medical device system comprising a processor configured to:

determine that a patient is in a first sleep stage during a first period of time,
determine a first seizure state of the patient, wherein the first seizure state of the patient comprises a seizure state of the patient during the first period of time, and
generate a first seizure probability metric for the first sleep stage based on at least the first sleep stage and the first seizure state.

13. The system of claim 12, wherein the processor determines a first seizure state of the patient by at least determining the first seizure state of the patient based on a bioelectrical brain signal of the patient sensed by a medical device.

14. The system of claim 12, wherein the processor is configured to:
determine that the patient is in a second sleep stage during a second period of time;
determine a second seizure state of the patient, wherein the second seizure state of the patient comprises a seizure state of the patient during the second period of time;
generate a second seizure probability metric for the second sleep stage based on at least the second sleep stage and the second seizure state; and
create a seizure probability profile for the patient based on at least the first and second seizure probability metrics.

15. The system of claim 14, wherein the seizure probability profile for the patient comprises the first and second seizure probability metrics.

16. The system of claim 12, wherein the processor determines the first seizure state of the patient by at least evaluating a bioelectrical brain signal of the patient via a seizure detection algorithm to determine whether the patient experienced a seizure during the first period of time.

17. The system of claim 16, wherein the processor is configured to adjust the seizure detection algorithm based on at least the first seizure probability metric.

18. The system of claim 12, wherein the processor is configured to:
deliver therapy to the patient to treat a seizure disorder of the patient; and
adjust at least one parameter of the therapy based on the first seizure probability metric.

19. The system of claim 18, wherein the processor adjusts at least one parameter of the therapy based on the first seizure probability metric by at least suspending the delivery of therapy when the patient occupies the first sleep stage.

20. The system of claim 12, wherein the sleep stage comprises an N1 sleep stage, an N2 sleep stage, a Deep Sleep stage, a rapid eye movement (REM) sleep stage, or an awake stage.

21. The system of claim 12, wherein the processor generates the first seizure probability metric by at least generating a metric indicative of susceptibility of the patient to seizure events during the first sleep stage.

22. The system of claim 12, wherein the processor is configured to:
determine that the patient is in the first sleep stage during a second period of time;
determine a second seizure state of the patient, wherein the second seizure state of the patient comprises a seizure state of the patient during the second period of time; and
adjust the first seizure probability metric for the first sleep stage based on at least the second seizure state.

23. A system comprising:
means for determining that a patient is in a first sleep stage during a first period of time;

means for determining a first seizure state of the patient, wherein the first seizure state of the patient comprises a seizure state of the patient during the first period of time; and means for generating a first seizure probability metric for the first sleep stage based on at least the first sleep stage and the first seizure state.

24. The system of claim 23, further comprising:

means for determining that the patient is in a second sleep stage during a second period of time;

means for determining a second seizure state of the patient, wherein the second seizure state of the patient comprises a seizure state of the patient during the second period of time;

means for generating a second seizure probability metric for the second sleep stage based on at least the second sleep stage and the second seizure state; and means for creating a seizure probability profile for the patient based on at east the first and second seizure probability metrics.

25. The system of claim 23, further comprising:

means for delivering therapy to the patient to treat a seizure disorder of the patient; and means for adjusting at least one parameter of the therapy based on the first seizure probability metric.

26. The system of claim 23, further comprising:

means for determining that the patient is in the first sleep stage during a second period of time;

means for determining a second seizure state of the patient, wherein the second seizure state of the patient comprises a seizure state of the patient during the second period of time; and means for adjusting the first seizure probability metric for the first sleep stage based on at east the second seizure state.

* * * * *

UNITED STATES PATENT AND TRADEMARK OFFICE
CERTIFICATE OF CORRECTION

PATENT NO. : 8,812,098 B2
APPLICATION NO. : 13/447460
DATED : August 19, 2014
INVENTOR(S) : Giftakis et al.

It is certified that error appears in the above-identified patent and that said Letters Patent is hereby corrected as shown below:

In the Claims

Col. 38, Line 2: "based on at east the first and second" should read --based on at least the first and second--

Col. 38, Line 16: "sleep stage based on at east the second" should read --sleep stage based on at least the second--

Signed and Sealed this
Twenty-first Day of April, 2015

Michelle K. Lee
*Director of the United States Patent and Trademark Office*